(12) United States Patent  
Rao et al.

(10) Patent No.: US 7,217,678 B2
(45) Date of Patent: May 15, 2007

(54) COBALT-SUBSTITUTED CHROMIUM OXIDE COMPOSITIONS, THEIR PREPARATION, AND THEIR USE AS CATALYSTS AND CATALYST PRECURSORS

(75) Inventors: Velliyur Nott Mallikarjuna Rao, Wilmington, DE (US); H. David Rosenfeld, Drumore, PA (US); Allen C. Sievert, Elkton, MD (US); Shekhar Subramoney, Hockessin, DE (US); Munirpallam Appadorai Subramanian, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1 day.

(21) Appl. No.: 10/523,228

(22) PCT Filed: Aug. 21, 2003

(86) PCT No.: PCT/US03/26326

§ 371 (c)(1),
(2), (4) Date: Jan. 31, 2005

(87) PCT Pub. No.: WO2004/018093

PCT Pub. Date: Mar. 4, 2004

(65) Prior Publication Data

US 2005/0228202 A1    Oct. 13, 2005

Related U.S. Application Data

(60) Provisional application No. 60/405,220, filed on Aug. 22, 2002.

(51) Int. Cl.
*B01J 27/06* (2006.01)
*B01J 23/00* (2006.01)

(52) U.S. Cl. .............. 502/224; 502/305; 502/319
(58) Field of Classification Search ............ 502/305, 502/319, 224
See application file for complete search history.

(56) References Cited

U.S. PATENT DOCUMENTS

| | | | |
|---|---|---|---|
| 3,258,500 A | | 6/1966 | Swamer et al. |
| 3,873,471 A | | 3/1975 | Koberstein et al. |
| 3,978,145 A | | 8/1976 | Knaak |
| 3,992,325 A | | 11/1976 | Knaak |
| 4,843,181 A | | 6/1989 | Gumprecht et al. |
| 5,036,036 A | | 7/1991 | Lerou |
| 5,057,634 A | | 10/1991 | Webster et al. |
| 5,155,082 A | | 10/1992 | Tung et al. |
| 5,177,273 A | * | 1/1993 | Bruhnke et al. ............ 570/169 |
| 5,185,482 A | | 2/1993 | Manzer et al. |
| 5,345,017 A | | 9/1994 | Rao et al. |
| 5,446,215 A | | 8/1995 | Cook et al. |
| 5,463,151 A | | 10/1995 | Cuzzato et al. |
| 5,494,873 A | * | 2/1996 | Tsuji et al. ................. 502/319 |
| 5,559,069 A | | 9/1996 | Rao et al. |
| 5,763,698 A | | 6/1998 | Manzer et al. |
| 6,274,780 B1 | * | 8/2001 | Rao et al. .................... 570/163 |
| 6,403,524 B2 | * | 6/2002 | Scott et al. .................. 502/307 |
| 6,503,865 B1 | * | 1/2003 | Kanemura et al. .......... 502/224 |
| 6,706,935 B2 | | 3/2004 | Manzer et al. |
| 2001/0011061 A1 | | 8/2001 | Scott et al. |
| 2002/0006374 A1 | * | 1/2002 | Kourtakis et al. ........ 423/418.2 |

FOREIGN PATENT DOCUMENTS

| | | |
|---|---|---|
| AU | A-29972/92 | 6/1993 |
| AU | A-80340/94 | 6/1995 |
| CN | 1048699 A | 1/1991 |
| CN | 1059334 A | 3/1992 |
| EP | 0365296 A1 | 4/1990 |
| EP | 0 486 333 | 5/1992 |
| EP | 0 641 598 A2 | 3/1995 |
| EP | 1 038 858 A1 | 9/2000 |
| JP | 04-262372 | 9/1992 |
| WO | WO 92/02476 | 2/1992 |
| WO | WO 2004/018095 A1 | 3/2004 |
| WO | WO 2004/018396 A1 | 3/2004 |

| WO | WO 2004/018397 | 3/2004 |

OTHER PUBLICATIONS

U.S. Appl. No. 10/523,227, filed Jan. 31, 2005, Nappa et al.
U.S. Appl. No. 10/523,223, filed Jan. 31, 2005, Rao et al.
U.S. Appl. No. 10/523,226, filed Jan. 31, 2005, Nappa et al.
Music et. al., Formation and Characterization of the Solid Solutions, J. Materials Science, 1996, pp. 4067-4076, vol. 31.
Chemical Abstract vol. 118:9 397, vol. 118, p. 138 (1993).

\* cited by examiner

*Primary Examiner*—J. A. Lorengo
*Assistant Examiner*—Patricia L. Hailey

(57) ABSTRACT

A crystalline alpha-chromium oxide where from about 0.05 atom % to about 6 atom % of the chromium atoms in the alpha-chromium oxide lattice are replaced by trivalent cobalt ($Co^{+3}$) atoms is disclosed. Also disclosed is a chromium-containing catalyst composition comprising as a chromium-containing component the crystalline cobalt-substituted alpha-chromium oxide; and a method for preparing a composition comprising the crystalline cobalt-substituted alpha-chromium oxide. The method involves (a) co-precipitating a solid by adding ammonium hydroxide to an aqueous solution of a soluble cobalt salt and a soluble trivalent chromium salt that contains at least three moles of nitrate per mole of chromium in the solution and has a cobalt concentration of from about 0.05 mole % to about 6 mole % of the total concentration of cobalt and chromium in the solution; and after at least three moles E of ammonium per mole of chromium in the solution has been added to the solution, (b) collecting the co-precipitated solid formed in (a); (c) drying the collected solid; and (d) calcining the dried solid. Also disclosed is a chromium-containing catalyst composition comprising a chromium-containing component prepared by treating the crystalline cobalt-substituted alpha-chromium oxide with a fluorinating agent; and a process for changing the fluorine distribution (i.e., content and/or arrangement) in a hydrocarbon or halogenated hydrocarbon in the presence of a catalyst. The process involves using as the catalyst a composition comprising the crystalline cobalt-substituted alpha-chromium oxide and/or the treated cobalt-substituted alpha-chromium oxide.

17 Claims, 4 Drawing Sheets

COBALT-SUBSTITUTED CHROMIUM OXIDE COMPOSITIONS, THEIR PREPARATION, AND THEIR USE AS CATALYSTS AND CATALYST PRECURSORS

This application represents a national filing under 35 U.S.C. 371 of International Application No. PCT/US2003/026326 filed Aug. 21, 2003 and claims priority of U.S. application Ser. No. 60/405,220 filed Aug. 22, 2002.

FIELD OF THE INVENTION

This invention relates to chromium-containing compositions and their preparation and use for the catalytic processing of hydrocarbons and/or halogenated hydrocarbons.

BACKGROUND

It is well known that $\alpha$-$Cr_2O_3$ and $\alpha$-$Fe_2O_3$ have in common the structure of $\alpha$-$Al_2O_3$ (corundum) with the $M^{+3}$ ions occupying octahedral sites in the hexagonally close-packed oxide lattice. In contrast, CoO has a lattice similar to NaCl while $CO_3O_4$ has a normal spinel structure. These basic structures are described in standard treatises; see, for example, pages 538, 543–545, and 550 of *Structural Inorganic Chemistry* by A. F. Wells, 5$^{th}$ ed. Clarendon Press, Oxford, UK (1986). $\gamma$-Chromium oxide ($CrO_{2.44}$) is described in Wilhelmi, *Acta Chemica Scandinavica*, Vol. 22, pages 2565–2573 (1968).

Numerous mixed metal oxides have been prepared in which the cation sites of the lattice are occupied by different metal ions. For example, solid solutions of the type ($Cr_x Fe_{1-x})_2O_3$ are known where $0<x<1$. These materials have been prepared by standard ceramic or sol-gel techniques as described by Music, et al. in *J. Materials Science*, Vol. 31, pages 4067–4076 (1996) and by Bhattacharya, et al. in *J. Materials Science*, Vol. 32, pages 577–560 (1997).

Mixed Cr—Co oxides having a spinel structure are known (see e.g., Bracconi et al. in *Ann. Chim. Fr.*, Vol. 4, pages 331–338 (1979) and Hanck and Laitinen in *J. Inorg. Nucl. Chem.*, Volume 33, pages 63–73 (1971)).

$CrCoO_3$ is referenced as an interconnector material in a fuel cell assembly (see Chem. Abs. 118:9397). Various mixed metal oxides containing cobalt and chromium are also disclosed in Castiglioni, et al., *J. Solid State Chemistry*, Vol. 152, 526–532 (2000); Nowotny et al., *J. Am. Ceram. Soc.*, Vol. 65, pages 192–196 (1982); and Zhang et al., *Journal of Power Sources*, Vol. 83, pages 121–127 (1999).

Certain metal oxides are used as catalysts and/or catalyst precursors in the manufacture of fluorinated hydrocarbons. Chromium(III) oxide in particular is useful as it has been found that it may be fluorinated by HF at elevated temperature to a give mixture of chromium fluoride and chromium oxyfluoride species which are active catalysts for conversion of C—Cl bonds to C—F bonds in the presence of HF. This conversion of C—Cl bonds to C—F bonds by the action of HF, known generally as halogen exchange, is a key step in many fluorocarbon manufacturing processes.

Chromium oxide compositions useful as catalyst precursors may be prepared in various ways or may take various forms. Chromium oxide suitable for vapor phase fluorination reactions may be prepared by reduction of Cr(VI) trioxide, by dehydration of Guignet's green, or by precipitation of Cr(III) salts with bases (see U.S. Pat. No. 3,258, 500). Another useful form of chromium oxide is hexagonal chromium oxide hydroxide with low alkali metal ion content as disclosed in U.S. Pat. No. 3,978,145. Compounds such as $MF_4$ (M=Ti, Th, Ce), $MF_3$ (M=Al, Fe, Y), and $MF_2$ (M=Ca, Mg, Sr, Ba, Zn) have been added to hexagonal chromium oxide hydroxide to increase catalyst life as disclosed in U.S. Pat. No. 3,992,325. A form of chromium oxide that is a precursor to a particularly active fluorination catalyst is that prepared by pyrolysis of ammonium dichromate as disclosed in U.S. Pat. No. 5,036,036.

The addition of other compounds (e.g., other metal salts) to supported and/or unsupported chromium-based fluorination catalysts has been disclosed. Australian Patent Document No. AU-A-80340/94 discloses bulk or supported catalysts based on chromium oxide (or oxides of chromium) and at least one other catalytically active metal (e.g., Mg, V, Mn, Fe, Co, Ni, or Zn), in which the major part of the oxide(s) is in the crystalline state (and when the catalyst is a bulk catalyst, its specific surface, after activation with HF, is at least 8 $m^2/g$). The crystalline phases disclosed include $Cr_2O_3$, $CrO_2$, $NiCrO_3$, $NiCrO_4$, $NiCr_2O_4$, $MgCrO_4$, $ZnCr_2O_4$ and mixtures of these oxides. Australian Patent Document AU-A-29972/92 discloses a mass catalyst based on chromium and nickel oxides in which the Ni/Cr atomic ratio is between 0.05 and 5. U.S. Patent Application Publication No. 2001/0011061 A1 discloses chromia-based fluorination catalysts (optionally containing Mg, Zn, Co, and Ni) in which the chromia is at least partially crystalline. Fluorinated catalysts containing cobalt and chromium in combination (e.g. impregnated on a support) are among those disclosed in U.S. Pat. No. 5,185,482. U.S. Pat. No. 5,559, 069 discloses homogeneously dispersed multiphase catalyst compositions characterized by dispersed phases of certain divalent metal fluorides (certain fluorides of Mn, Co, Zn, Mg, and/or Cd) and certain trivalent metal fluorides (fluorides of Al, Ga, V, and/or Cr).

There remains a need for halogen exchange catalysts that can be used for processes such as the selective fluorination and chlorofluorination of saturated and unsaturated hydrocarbons, hydrochlorocarbons, hydrochlorofluorocarbons, and chlorofluorocarbons, the fluorination of unsaturated fluorocarbons, the isomerization and disproportionation of fluorinated organic compounds, the dehydrofluorination of hydrofluorocarbons, and the chlorodefluorination of fluorocarbons.

SUMMARY OF THE INVENTION

This invention provides a crystalline alpha-chromium oxide where from about 0.05 atom % to about 6 atom % of the chromium atoms in the alpha-chromium oxide lattice are replaced by trivalent cobalt ($Co^{+3}$) atoms, and a chromium-containing catalyst composition comprising as a chromium-containing component said crystalline cobalt-substituted alpha-chromium oxide.

This invention also provides a method for preparing a composition comprising said crystalline cobalt-substituted alpha-chromium oxide. The method comprises (a) co-precipitating a solid by adding ammonium hydroxide (aqueous ammonia) to an aqueous solution of a soluble cobalt salt and a soluble trivalent chromium salt that contains at least three moles of nitrate (i.e., $NO_3^-$) per mole of chromium (i.e., $Cr^{3+}$) in the solution and has a cobalt concentration of from about 0.05 mole % to about 6 mole % of the total concentration of cobalt and chromium in the solution; and after at least three moles of ammonium (i.e., $NH_4^+$) per mole of chromium (i.e., $Cr^{3+}$) in the solution has been added to the solution, (b) collecting the co-precipitated solid formed in (a); (c) drying the collected solid; and (d) calcining the dried solid.

This invention also provides a chromium-containing catalyst composition comprising a chromium-containing component prepared by treating said crystalline cobalt-substituted alpha-chromium oxide with a fluorinating agent (e.g., hydrogen fluoride).

This invention also provides a process for changing the fluorine distribution (i.e., content and/or arrangement) in a hydrocarbon or halogenated hydrocarbon in the presence of a catalyst. The process is characterized by using as the catalyst a composition comprising at least one chromium-containing component selected from the group consisting of said crystalline cobalt-substituted alpha-chromium oxides and said treated cobalt-substituted alpha-chromium oxides.

DETAILED DESCRIPTION

Figure 1:
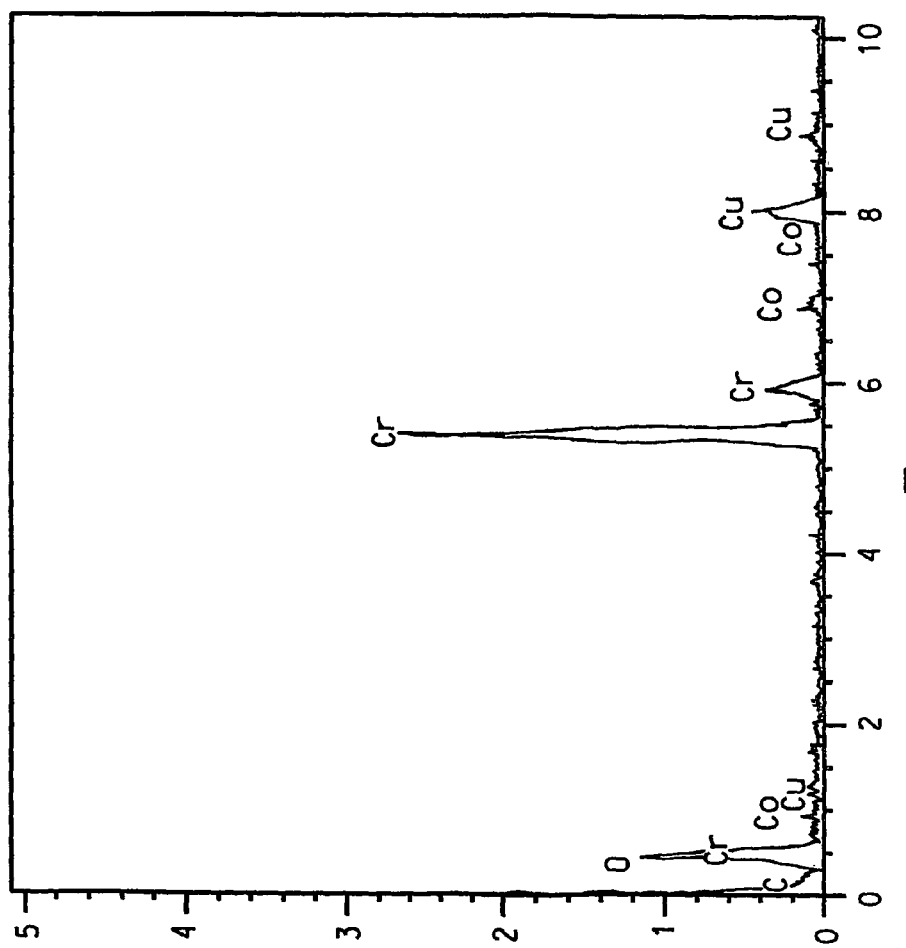
FIG. 1 represents an energy dispersive spectroscopy spectrum for a sample of cobalt-substituted alpha-chromium oxide nominally containing 2 atom % cobalt.

New compositions of this invention comprise cobalt-substituted alpha-chromium oxide containing from about 0.05 atom % to about 6 atom % cobalt based on the total of the cobalt and chromium in the alpha-chromium oxide which retains the corundum structure. This invention includes a catalytic composition comprising said crystalline cobalt-substituted $\alpha$-$Cr_2O_3$. The crystalline cobalt-substituted alpha-chromium oxides have the general formula $\alpha$-$Co_xCr_{2-x}O_3$ where $x=0.001-0.12$.

The compositions of the present invention may be prepared by the method described above using co-precipitation. In the typical co-precipitation technique, an aqueous solution of cobalt(II) or cobalt(III) salts and chromium(III) salts is prepared. The relative concentrations of cobalt and chromium(III) salts in the aqueous solution is dictated by the bulk mole percent cobalt relative to chromium desired in the final catalyst. The concentration of chromium(III) in the aqueous solution is typically in the range of from 0.3 to 3 molar (moles per liter) with 0.75–1.5 molar being a preferred concentration. Chromium(III) salts suitable for preparation of the aqueous solution are the nitrate, sulfate, acetate, formate, oxalate, phosphate, bromide, and chloride and various hydrated forms of these salts. Other chromium(III) salts that are useful for the preparation of the aqueous solutions include hexacoordinate complexes of the formula $[CrL_{6-z}A_z]^{+3-z}$ where each L is a neutral (i.e., uncharged) ligand selected from the group consisting of $H_2O$, $NH_3$, $C_1$–$C_4$ primary, secondary, or tertiary organic amines, a $C_1$–$C_4$ alkyl nitrites, or pyridine, where each A is an anionic ligand selected from the group consisting of fluoride, chloride, bromide, iodide, hydroxide, nitrite, and nitrate, and where z has a value of from 0 to 3 inclusive. Included are neutral bidentate ligands such as ethylene diamine which are equivalent to two L in that they may occupy two coordination sites. Also included are anionic bidentate ligands such as $C_1$–$C_4$ carboxylate which may occupy two coordination sites. Also included are dianionic ligands such as sulfate which are equivalent to two A ligands and may occupy more than one coordination site.

Salts containing alkali metals such as chromium potassium sulfate are not preferred because the presence of alkali metals can hinder catalyst activity (see U.S. Pat. No. 4,843,181). Chromium(VI) precursors, such as $CrO_3$, though not preferred, may be used but require reduction to Cr(III) with a compound such as ethanol before precipitation.

Chromium(III) nitrate, or its hydrated forms such as $[Cr(NO_3)_3(H_2O)_9]$, are the most preferred chromium(III) salt for preparation of said aqueous solution.

Cobalt(II) salts suitable for preparation of the aqueous solution are the nitrate, sulfate, formate, oxalate, bromide, and chloride and various hydrated forms of these salts. Salts containing alkali metals such as cobalt potassium bis(sulfate) are not preferred because the presence of alkali metals can hinder catalyst activity. Cobalt(II) nitrate hydrate (e.g., $[Co(NO_3)_2(H_2O)_6]$) is the most preferred cobalt(II) salt.

Cobalt(III) salts that are useful for the preparation of the aqueous solutions include hexacoordinate complexes of the formula $[CoL_{6-z}A_z]^{+3-z}$ where each L is a neutral (i.e., uncharged) ligand selected from the group consisting of $H_2O$, $NH_3$, $C_1$–$C_4$ primary, secondary, or tertiary organic amine, a $C_1$–$C_4$ alkyl nitrite, or pyridine, where each A is an anionic ligand selected from the group consisting of fluoride, chloride, bromide, iodide, hydroxide, nitrite, and nitrate, and where a has a value of from 0 to 3 inclusive. Included are neutral bidentate ligands such as ethylene diamine which are equivalent to two L in that they may occupy two coordination sites. Also included are anionic bidentate ligands such as $C_1$–$C_4$ carboxylate which may occupy two coordination sites. Also included are dianionic ligands such as sulfate which are equivalent to two A ligands and may occupy more than one coordination site. Preferred cobalt(III) starting materials are hexammine salts (e.g., $[Co(NH^3)_6]^{+3}$ where the counter ion is chloride or nitrate. Hexaamminecobalt(III) chloride (e.g., $[Co(NH_3)_6]Cl_3]$) is the most preferred cobalt(III) salt.

The aqueous solution of the cobalt salts and chromium (III) salts may then be evaporated either under vacuum or at elevated temperature to give a solid which is then calcined.

Preferably, however, the aqueous solution of the cobalt salts and chromium(III) salts is then treated with a base such as ammonium hydroxide (aqueous ammonia) to precipitate cobalt and chromium as the hydroxides. Bases containing alkali metals such as sodium or potassium hydroxide or the carbonates may be used but are not preferred. The addition of ammonium hydroxide to the aqueous solution of cobalt and chromium(III) salts is typically carried out gradually over a period of 1 to 12 hours. The pH of the solution is monitored during the addition of base. The final pH is typically in the range of 6.0 to 11.0, preferably from about 7.5 to about 9.0, and most preferably from about 8.0 to 8.7. The precipitation of the cobalt hydroxide/chromium hydroxide mixture is typically carried out at a temperature of about 15° C. to about 60° C., preferably from about 20° C. to about 40° C. After the ammonium hydroxide is added, the mixture is typically stirred for up to 24 hours.

Of note are preparations where excess ammonium nitrate (i.e., more than three moles of ammonium nitrate per mole of chromium) is present in the aqueous solution. For example, in addition to the ammonium nitrate already present from reaction of ammonium hydroxide with chromium nitrate, from about 0.1 mole to about 7.0 moles of additional ammonium nitrate per mole of chromium may be added to the solution before, during, or after the co-precipitation of the compositions. Surprisingly, we have found that addition of excess ammonium nitrate to the precipitated mixture of cobalt and chromium hydroxides prior to the dehydration step may be used to decrease the particle size of the $\alpha$-Co$_x$Cr$_{2-x}$O$_3$ phase which in turn increases the surface area of that phase and the activity of the catalyst (see PREPARATION EXAMPLES 15, 17, and 18 and EXAMPLES 20, 21, 30, and 31).

After the ammonium nitrate is added to the mixture, it is preferably stirred for about 0.5 to ten hours (preferably for about one to five hours) at a temperature of from about 20° C. to about 60° C. The mixture is then dried and calcined as indicated below.

Other agents that serve this purpose include aqueous hydrogen peroxide (1% to 30% solutions), ozone, peroxy acids such as peroxyacetic acid, and ammonium persulfate. Agents such as halogens may be used but are not preferred. Agents containing alkali metals such as potassium persulfate or sodium perborate may also be used, but are not preferred.

After the precipitation of the mixture of cobalt and chromium hydroxides is complete, and the ammonium nitrate or other agents added if desired, the mixture is dried by evaporation.

Optionally, the precipitated cobalt and chromium hydroxide mixture may be collected and, if desired, washed with deionized water before drying. This may influence the activity of the catalyst (see Examples 32 and 33).

After the cobalt and chromium hydroxide mixture has been dried, the nitrate salts are then decomposed by heating the solid from about 250° C. to about 350° C. The resulting solid is then calcined at temperature of from about 375° C. to about 1000° C., preferably from about 400° C. to about 600° C. The calcination temperature can influence the activity of the catalysts and, in turn, the product distribution when the catalysts are used to change the fluorine distribution in hydrocarbons and halogenated hydrocarbons (see Examples 34 and 35). Lower calcination temperatures may result in the presence of some residual nitrate impurities.

The calcination is preferably carried out in the presence of oxygen, most preferably in the presence of air.

The metal oxide compositions of this invention may be characterized by well-established analytical techniques including X-Ray absorption spectroscopy (XAS), X-ray powder diffraction (XRD), transmission electron microscopy (TEM), and energy dispersive spectroscopy (EDS). EDS is an analytical tool available in conjunction with scanning or analytical TEM.

After calcination, the resulting cobalt-substituted crystallites are not visually distinguishable from $\alpha$-Cr$_2$O$_3$ by TEM. Furthermore, X-ray and electron diffraction studies are entirely consistent with the $\alpha$-Cr$_2$O$_3$ structure with some lattice contraction proportional to the amount of Co(III) substituted for Cr(III) in the structure. The compositions are therefore concluded to have the general formula $\alpha$-Co$_x$Cr$_{2-x}$O$_3$ where $x=0.001-0.12$.

Figure 2:
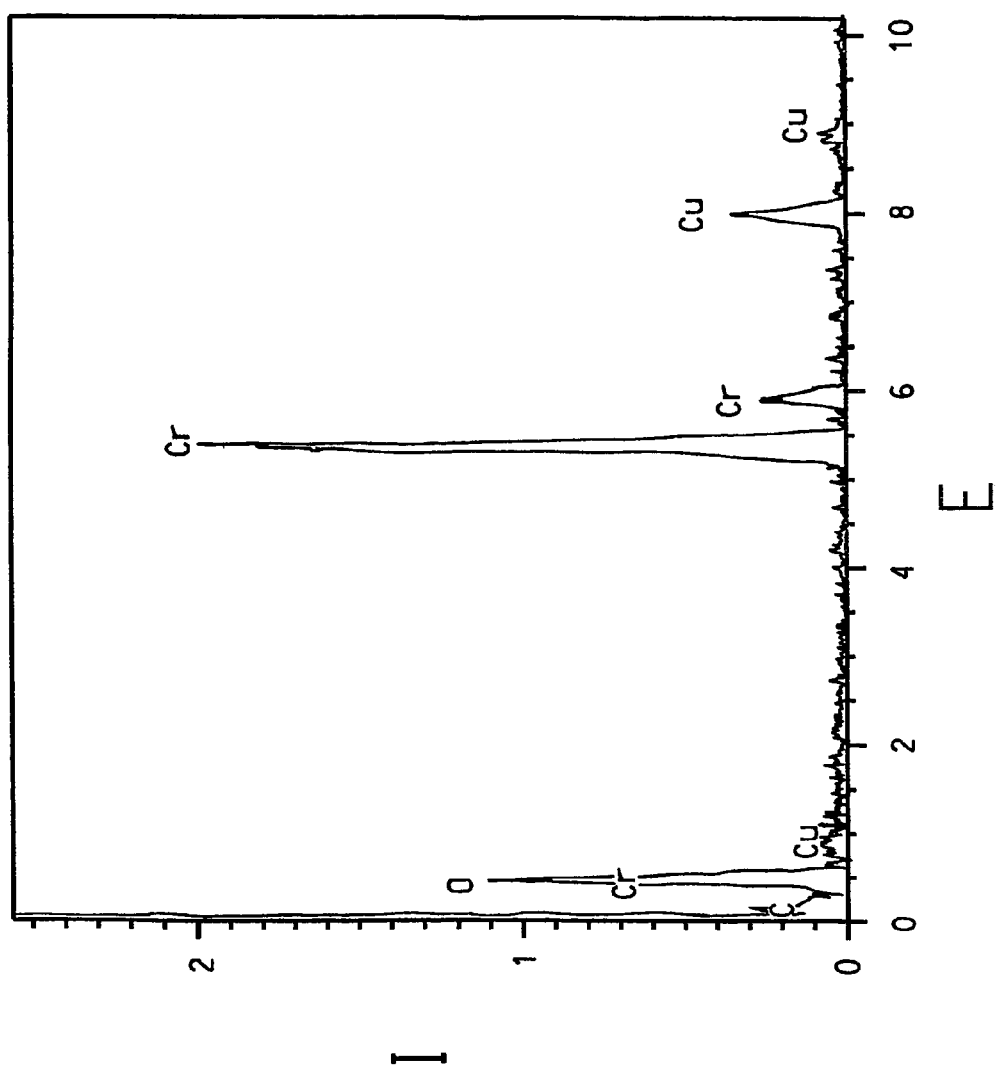
FIG. 2 represents an energy dispersive spectroscopy spectrum for a sample of alpha-chromium oxide without cobalt substitution.
Figure 3:
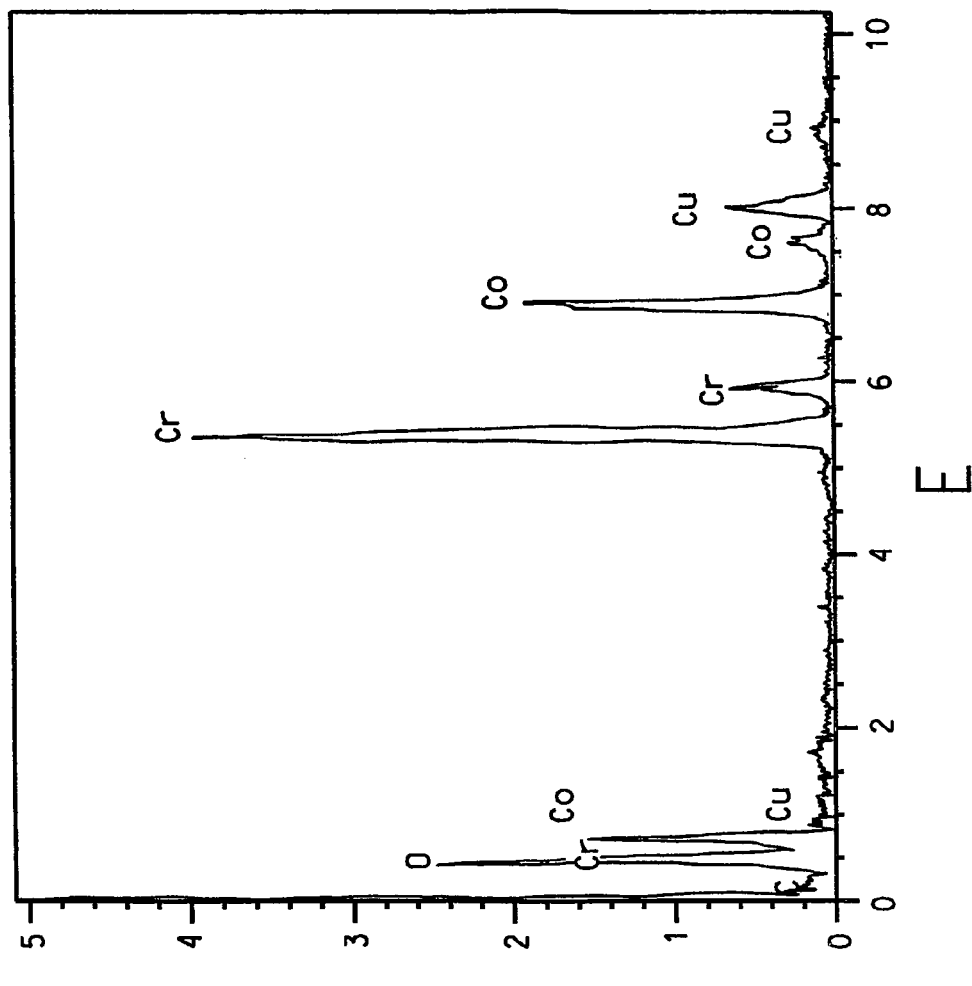
FIG. 3 represents an energy dispersive spectroscopy spectrum for a sample of cobalt chromium spinel.

The presence of cobalt in the various cobalt/chromium compositions of this invention is clearly indicated by elemental analysis using EDS. FIG. 1 shows the EDS spectrum of a sample of a cobalt-substituted $\alpha$-Cr$_2$O$_3$ nominally containing 2 atom % Co. For comparison, FIG. 2 shows the EDS spectrum of $\alpha$-Cr$_2$O$_3$ without cobalt substitution and FIG. 3 shows the EDS spectrum of commercially available CoCr$_2$O$_4$, a cobalt chromium spinel. In each of these three figures X-ray intensity, I, representing thousands of counts is plotted against energy level, E, representing thousands of electron volts (keV). Peaks in each plot correlate with the presence of certain elements. The presence of cobalt is clearly indicated in the EDS spectrum in FIG. 1 while the cobalt peaks are absent in FIG. 2. At higher loadings of cobalt (e.g., compositions having a bulk composition of cobalt greater than about 6 atom % cobalt based on the total metal content), a second spinel-like phase with a nominal composition (Cr$_{0.5}$CO$_{0.5}$)$_3$O$_4$ and with a crystallite size in the range of 10 nm can be easily identified by TEM and EDS. The relative heights of 2:1 for the K$_\alpha$ peaks of Cr (atomic mass 52) and Co (atomic mass 59), respectively, in FIG. 3 indicate that the EDS data are valid on a quantitative basis.

XAS and XRD data were obtained for compositions that were nominally 100% Cr (no cobalt added), Cr98%/Co2%, Cr95%/Co5%, and Cr90%/Co10%. XAS and XRD analysis clearly show that cobalt is substituted into $\alpha$-Cr$_2$O$_3$. XRD results for Cr98% Co2% are shown in Table 1. Diffraction peaks having d-spacings of 3.1368, 1.9211, 1.3581, 1.2464, and 1.1088 are due to a silicon internal standard added to the sample for calibration of the diffractometer. All other diffraction peaks can be indexed to the $\alpha$-Cr$_2$O$_3$ structure with a slightly reduced unit cell volume.

TABLE 1

XRD Results for a Co-Substituted alpha-Cr$_2$O$_3$ Composition that is Nominally 98 atom % Cr/2 atom % Co

| d (Angstroms) | Height | FWHM[a.] |
| --- | --- | --- |
| 3.6263 | 134 | 0.627 |
| 3.1368 | 2539 | 0.135 |
| 2.6635 | 288 | 0.607 |
| 2.4656 | 668 | 0.448 |
| 2.2550 | 53 | 0.312 |
| 2.1661 | 292 | 0.450 |
| 2.0430 | 16 | 0.469 |
| 1.9211 | 1842 | 0.136 |
| 1.8105 | 128 | 0.634 |
| 1.6654 | 707 | 0.510 |
| 1.6382 | 1076 | 0.223 |
| 1.5772 | 37 | 0.202 |
| 1.4644 | 98 | 0.533 |
| 1.4260 | 289 | 0.579 |
| 1.3581 | 274 | 0.195 |
| 1.2907 | 92 | 0.762 |
| 1.2464 | 460 | 0.159 |
| 1.2352 | 55 | 0.566 |
| 1.2055 | 44 | 0.516 |
| 1.1486 | 40 | 0.283 |
| 1.1238 | 38 | 0.362 |
| 1.1088 | 689 | 0.162 |
| 1.1059 | 272 | 0.215 |

[a.]FWHM means full width at half maximum.

If Co substitutes for Cr in the $\alpha$-Cr$_2$O$_3$ phase, it is expected to be in octahedral coordination (N Co—O=6) and in the 3+ oxidation state. XAS results from the Cr—K edge of the samples indicate that all Cr is present as Cr$^{3+}$ and is octahedrally coordinated. If the cobalt is present in the spinel-like phase observed by electron microscopy, some of these atoms will have tetrahedral coordination and be present in the +2 oxidation state.

Figure 4:
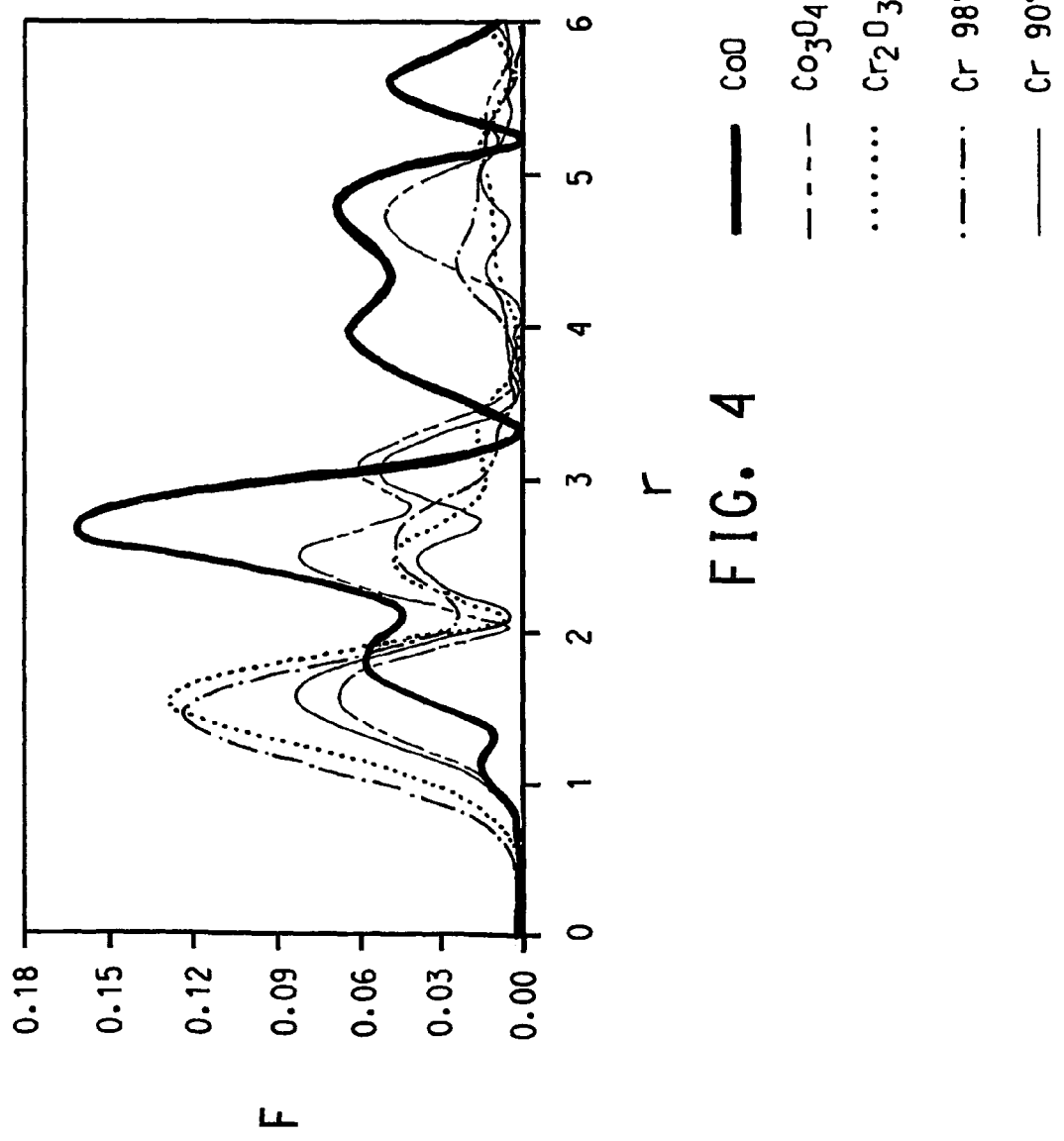
FIG. 4 represents a plot of the radial distribution function (i.e., the probability of finding an atom at a certain distance, r, from a central atom) associated with the local atomic structure around (a) a cobalt central atom in CoO, (b) a cobalt central atom in $Co_3O_4$, (c) a chromium central atom in $Cr_2O_3$, (d) cobalt in a sample of cobalt-substituted alpha-chromium oxide nominally containing 2 atom % cobalt and (e) cobalt in a sample of cobalt-substituted alpha-chromium oxide nominally containing 10 atom % cobalt.

FIG. 4 shows the radial distribution function (RDF) for five materials. The radial distribution function represents the probability of finding an atom at a certain distance, r, from a central atom. These probabilities are weighted by factors that depend on the type of atom. Thus an RDF is a representation of local atomic structure around the central atom. An RDF is obtained by Fourier transform of the extended x-ray absorption fine structure (EXAFS) data, and may be represented by a plot of the dimensionless Fourier transform magnitude, F, versus the pair separation distance in angstroms. In simplified terms, one might view a peak in an RDF plot as indicative of a distance at which there is a coordination sphere around the central atom. A small difference is expected between the actual separation distance and the "r" shown in a plot when no correction is made to account for the phase shift on backscattering of excited electrons. In FIG. 4, F is plotted against the pair separation distance, r (shown in angstroms, uncorrected for phase shift) for each of the five materials. Included in FIG. 4 are curve A representing the local structure around cobalt in CoO, curve B representing the local structure around cobalt in $Co_3O_4$, curve C representing the local structure around chromium in $\alpha$-$Cr_2O_3$. Also included in FIG. 4 is curve D representing the local structure around cobalt in the cobalt-substituted alpha-chromium oxide with a nominal composition of 98% chromium and 2% cobalt, and curve E representing the local structure around cobalt in the cobalt-substituted alpha-chromium oxide with a nominal composition of 90% chromium and 10% cobalt. No spinel phase was detected by electron microscopy in this sample, so all the Co is considered to be associated with the $\alpha$-$Cr_2O_3$ phase, either as a separate cobalt oxide coating, or as a substitute for Cr in the $\alpha$-$Cr_2O_3$ lattice. The curve in FIG. 4 representing the local structure around cobalt in the cobalt-substituted alpha-chromium oxide with a nominal composition of 98% chromium and 2% cobalt, indicates that the local atomic structure around Co in this sample bears no resemblance to that of expected common cobalt oxide phases, but is very similar to that of Cr in the $\alpha$-$Cr_2O_3$ phase.

Table 2 shows average first near neighbor coordination numbers (N Co—O) and average Co oxidation states obtained from XAS analysis of the Co K edge absorption spectra as well as unit cell volumes for the $\alpha$-$Cr_2O_3$-like phase obtained by XRD.

TABLE 2

Characterization of Metal-Substituted alpha-Chromium(III) Oxide

| Composition | Cr/Co atom % | Average N (Co—O) | Average Co Oxid. State | UnitCell Volume ($nm^3$) |
|---|---|---|---|---|
| Cr100% | 100/0 | | | 0.284839 |
| Cr98% Co2% | 98/2 | 6.01 | 2.940 | 0.284614 |
| Cr95% Co5% | 95/5 | 5.67 | 2.840 | 0.284268 |
| Cr90% Co10% | 90/10 | 5.46 | 2.634 | 0.284177 |

The reduction in unit cell volume on introduction of Co can be understood by consideration of ionic radii. If $Co^{+3}$ substitute into the octahedral environment of $Cr^{+3}$ in $\alpha$-$Cr_2O_3$, they will adopt a low spin configuration as discussed by Cotton in chapter 8 of *Chemical Applications of Group Theory*, 3rd ed. (New York, Wiley, 1990). Using ionic radii of high spin $Cr^{+3}$ (62 pm), low spin $Co^{+3}$ (53 pm), and $O^{-2}$ (137 pm) as given by Shannon and Prewift in *Acta Crystallographica*, Volume B25, pages 925 to 945 (1969), the unit cell volume contraction may be related to the amount of low spin $Co^{+3}$ substituted for high spin $Cr^{+3}$ in the $\alpha$-$Cr_2O_3$ lattice. These relationships are summarized in Table 3 which shows the amount of cobalt actually substituted into the $\alpha$-$Cr_2O_3$ phase for the four Co-substituted compositions based on coordination numbers, oxidation states, and unit cell volumes. The data in Table 3 are in good agreement and suggest a solubility limit of cobalt in the $\alpha$-$Cr_2O_3$ phase of about 6 atom %. Further indication of the cobalt solubility limitation for bulk cobalt concentrations above 6 atom % is provided by the curve in FIG. 4 which represents the local structure around cobalt in the cobalt-substituted alpha-chromium oxide with a nominal composition of 90% chromium and 10% cobalt. This curve suggests that some of the cobalt is present as $Co_3O_4$.

TABLE 3

Amount of Cobalt Substituted into $\alpha$-$Cr_2O_3$ Lattice for Various Compositions

| | atom % Co Substituted into alpha-$Cr_2O_3$ Lattice | | |
|---|---|---|---|
| Composition | Based on N (Co—O) | Based on Co Oxid'n State | Based on Unit Cell Vol. |
| Cr98%/Co2% | 2.00 (0.15) | 1.82 (0.03) | 1.72 (0.4) |
| Cr95%/Co5% | 3.75 (0.38) | 3.80 (0.08) | 4.37 (0.4) |
| Cr90%/Co10% | 5.94 (0.75) | 4.51 (0.15) | 5.06 (0.4) |

Other phases such as chromium-cobalt spinel phases may be present in the chromium oxide compositions of the present invention. The presence of these phases having an overall stoichiometry of $(Cu_{0.5}Cr_{0.5})_3O_4$ was detected by EDS and TEM. These phases were normally minor relative to the $\alpha$-$Cr_2O_3$-like phase and usually had smaller particle sizes.

The surface area of the chromium oxide compositions of the present invention is typically in the range of about 1 to 100 $m^2$/gram. The $\alpha$-$Co_xCr_{2-x}O_3$ phase present in the compositions prepared by the process of this invention is typically made up of crystallites having a particle sizes varying from about 20 to about 400 nm, typically from about 40 to about 250 nm. Included in this invention are microcrystalline materials with particle sizes smaller than 20 nm.

The calcined chromium oxide compositions of the present invention may be formed into various shapes such as pellets, granules, and extrudates for use in packing reactors. It may also be used in powder form.

The cobalt content of the chromium oxide compositions of the present invention effects the activity of the catalyst obtained after fluorinating the mixed metal oxide. For example, in the chlorofluorination of $CCl_2$=$CClCF_3$ to $CF_3CClFCF_3$, the activity of the fluorinated metal oxide catalysts containing cobalt and chromium for formation of $CF_3CClFCF_3$ is improved for those compositions having 2–5 atom % cobalt in the catalyst relative to a chrome catalyst containing no cobalt (see TABLE 4). Furthermore, in accord with the teachings of this invention the activity of a composition containing a given ratio of cobalt to chromium may be enhanced by treating the initial solution of cobalt(II) and chromium(III) nitrates with an agent such as ammonium nitrate prior to dehydration and calcination.

TABLE 4

Activity of Fluorinated Cobalt/Chromium Oxides for Chlorofluorination of $CCl_2$=$CClCF_3$ to $CF_3CClFCF_3$[a.]

| Cr/Co Ratio | Calcination Temperature | % $CF_3CClFCF_3$ in Product at 400° C. |
|---|---|---|
| 100/0 | 400° C. | 24.1 |
| 99/1 | 400° C. | 47.4 |
| 98/2 | 400° C. | 46.6 |
| 98/2 | 550° C. | 36.7 |

TABLE 4-continued

Activity of Fluorinated Cobalt/Chromium Oxides for Chlorofluorination of $CCl_2=CClCF_3$ to $CF_3CClFCF_3{}^a$.

| Cr/Co Ratio | Calcination Temperature | % $CF_3CClFCF_3$ in Product at 400° C. |
|---|---|---|
| 97/3 | 400° C., washed | 31.7 |
| 95/5 | 400° C., excess $NH_4NO_3$ | 27.6[b.] |

[a.]Catalysts were prepared by co-precipitation technique using ammonia. Molar feed ratios of HF, 1213xa, and $Cl_2$ = 30:1:2.
[b.]Reactor temperature 350° C.

Cobalt chromium spinel is not considered an effective catalysts for fluorination or chlorofluorination reactions (see COMPARATIVE EXAMPLE 26).

The compositions of this invention may further comprise one or more additives in the form of metal compounds that alter the selectivity or activity of the crystalline cobalt-substituted alpha-chromium oxides or the fluorinated metal oxide catalysts containing cobalt and chromium. Suitable additives may be selected from the group consisting of fluorides, oxides, or oxyfluoride compounds of Mg, Ca, Sc, Y, La, Ti, Zr, Hf, V, Nb, Ta, Mo, W, Mn, Re, Fe, Ru, Co, Rh, Ir, Ni, Pd, Pt, Cu, Ag, Au, Ce, and Zn.

The total content of the additive(s) in the compositions of the present invention may be from about 0.05 atom % to about 15 atom % based on the total metal content of the compositions. The additives may be incorporated into the compositions of the present invention by standard procedures such as by impregnation.

Typically, the calcined compositions will be pre-treated with a fluorinating agent prior to use as catalysts for changing the fluorine distribution of hydrocarbons and/or halogenated hydrocarbon compounds. Typically this fluorinating agent is HF though other materials may be used such sulfur tetrafluoride, carbonyl fluoride, and fluorinated hydrocarbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process in the instant invention, and thereafter, passing HF over the dried, calcined catalyst so as to partially saturate the catalyst with HF. This is conveniently carried out by passing HF over the catalyst for a period of time, for example, about 0.1 to about 10 hours at a temperature of, for example, about 200° C. to about 450° C. Nevertheless, this pre-treatment is not essential.

As noted above catalysts provided in accordance with this invention may be used for changing the fluorine distribution in hydrocarbons and/or halogenated hydrocarbons. The fluorine distribution in a hydrocarbon or a halogenated hydrocarbon may be changed by increasing the fluorine content of the hydrocarbon or the halogenated hydrocarbon. The fluorine distribution of a halogenated hydrocarbon may also be changed by decreasing the fluorine content of the halogenated hydrocarbon and/or rearranging the placement of fluorine atoms on the carbon atoms of the halogenated hydrocarbon. Of note are processes where the fluorine distribution in halogenated hydrocarbons containing from one to twelve carbon atoms is changed, particularly processes where the fluorine distribution in halogenated hydrocarbons containing from one to six carbon atoms is changed. Also of note are processes where the fluorine content of hydrocarbons containing from one to twelve carbon atoms is increased, particularly processes where the fluorine content in hydrocarbons containing one to six carbon atoms is increased. Processes for changing the fluorine distribution in halogenated hydrocarbons include fluorination, chlorofluorination, isomerization, disproportionation, dehydrofluorination and chlorodefluorination. The processes of this invention are characterized by using as the catalyst a composition comprising at least one chromium-containing component selected from the group consisting of the crystalline cobalt-substituted alpha-chromium oxide described above and said cobalt-substituted alpha-chromium oxide which has been treated with a fluorinating agent. Typical of saturated halogenated hydrocarbons suitable for fluorination, chlorofluorination, isomerization, disproportionation, dehydrofluorination and chlorodefluorination processes are those which have the formula $C_nH_aBr_bCl_cF_d$, wherein n is an integer from 1 to 6, a is an integer from 0 to 12, b is an integer from 0 to 4, c is an integer from 0 to 13, d is an integer from 0 to 13, the sum of b, c and d is at least 1 and the sum of a, b, c, and d is equal to 2n+2, provided that n is at least 2 for isomerization, disproportionation and dehydrofluorination processes, a is at least one for dehydrofluorination processes, b is 0 for chlorodefluorination processes, b+c is at least 1 for fluorination processes and is 0 for dehydrofluorination processes, a+b+c is at least 1 for fluorination, chlorofluorination, isomerization, disproportionation and dehydrofluorination processes and d is at least 1 for isomerization, disproportionation, dehydrofluorination and chlorodefluorination processes. Typical of unsaturated halogenated hydrocarbons suitable for fluorination, chlorofluorination, isomerization, disproportiopnation, and chlorodefluorination processes are those which have the formula $C_pH_eBr_fCl_gF_h$, wherein p is an integer from 2 to 6, e is an integer from 0 to 10, f is an integer from 0 to 2, g is an integer from 0 to 12, h is an integer from 0 to 11, the sum of f, g and h is at least 1 and the sum of e, f, g, and h is equal to 2p, provided that f is 0 for chlorodefluorination processes, e+f+g is at least 1 for isomerization and disproportionation processes and h is at least 1 for isomerization, disproportionation and chlorodefluorination processes. Typical of saturated hydrocarbons suitable for chlorofluorination are those which have the formula $C_qH_r$ where q is an integer from 1 to 6 and r is 2q+2. Typical of unsaturated hydrocarbons suitable for fluorination and chlorofluorination are those which have the formula $C_iH_j$ where i is an integer from 2 to 6 and j is 2i.

Fluorination

Included in this invention is a process for increasing the fluorine content of a halogenated hydrocarbon compound or an unsaturated hydrocarbon compound by reacting said compound with hydrogen fluoride in the vapor phase in the presence of a catalyst composition comprising at least one chromium-containing component selected from the group consisting of the crystalline cobalt-substituted alpha-chromium oxide described above and said cobalt-substituted alpha-chromium oxide which has been treated with a fluorinating agent. The catalyst composition may optionally contain additional components such as additives to alter the activity and selectivity of the catalyst.

Halogenated hydrocarbon compounds suitable as starting materials for the fluorination process of this invention may be saturated or unsaturated. Saturated halogenated hydrocarbon compounds suitable for the fluorination processes of this invention include those of the general formula $C_nH_aBr_bCl_cF_d$, wherein n is an integer from 1 to 6, a is an integer from 0 to 12, b is an integer from 0 to 4, c is an integer from 0 to 13, d is an integer from 0 to 13, and the sum of a, b, c, and d is equal to 2n+2, provided that b+c is at least 1.

Unsaturated halogenated hydrocarbon compounds suitable for the fluorination processes of this invention include those of the general formula $C_pH_eBr_fCl_gF_h$, wherein p is an integer from 2 to 6, e is an integer from 0 to 10, f is an integer from 0 to 2, g is an integer from 0 to 12, h is an integer from 0 to 11, the sum of f, g and h is at least 1 and the sum of e, f, g, and h is equal to 2p. Unsaturated hydrocarbons suitable for fluorination are those which have the formula $C_iH_j$ where i is an integer from 2 to 6 and j is 2i. The fluorine content of saturated compounds of the formula $C_nH_aBr_bCl_cF_d$, unsaturated compounds of the formula $C_pH_eBr_fCl_gF_h$ and/or unsaturated compounds of the formula $C_iH_j$ may be increased by reacting said compounds with HF in the vapor phase in the presence of a catalyst composition comprising at least one chromium-containing component selected from the group consisting of the crystalline cobalt-substituted alpha-chromium oxide described above and said cobalt-substituted alpha-chromium oxide which has been treated with a fluorinating agent. Such a process is referred to herein as a vapor phase fluorination reaction.

The vapor phase fluorination reactions are typically conducted at temperatures of from about 150° C. to 500° C. For saturated compounds the fluorination is preferably carried out from about 175° C. to 400° C. and more preferably from about 200° C. to about 350° C. For unsaturated compounds the fluorination is preferably carried out from about 150° C. to 350° C. and more preferably from about 175° C. to about 300° C.

The vapor phase fluorination reactions are typically conducted at atmospheric and superatmospheric pressures. For reasons of convenience in downstream separations processes (e.g., distillation), pressures of up to about 30 atmospheres may be employed.

The vapor phase fluorination reactions are typically conducted in a tubular reactor. The reactor and its associated feed lines, effluent lines, and associated units should be constructed of materials resistant to hydrogen fluoride and hydrogen chloride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel.

The contact time in the reactor is typically from about 1 to about 120 seconds and preferably from about 5 to about 60 seconds.

The amount of HF reacted with the unsaturated hydrocarbons or halogenated hydrocarbon compounds should be at least a stoichiometric amount. The stoichiometric amount is based on the number of Br and/or Cl substituents to be replaced by F in addition to one mole of HF to saturate the carbon-carbon double bond if present. Typically, the molar ratio of HF to the said compounds of the formulas $C_nH_aBr_b Cl_cF_d$, $C_pH_eBr_fCl_gF_h$, and $C_iH_j$ can range from about 0.5:1 to about 100:1, preferably from about 2:1 to about 50:1, and more preferably from about 3:1 to about 20:1. In general, with a given catalyst composition, the higher the temperature and the longer the contact time, the greater is the conversion to fluorinated products. The above variables can be balanced, one against the other, so that the formation of higher fluorine substituted products is maximized.

Examples of saturated compounds of the formula $C_nH_aBr_b Cl_cF_d$ which may be reacted with HF in the presence of the catalyst of this invention include $CH_2Cl_2$, $CH_2Br_2$, $CHCl_3$, $CCl_4$, $C_2Cl_6$, $C_2BrCl_5$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, $C_2HClF_4$, $C_2HBrF_4$, $C_2H_2Cl_4$, $C_2H_2Cl_3F$, $C_2H_2Cl_2F_2$, $C_2H_2ClF_3$, $C_2H_3Cl_3$, $C_2H_3Cl_2F$, $C_2H_3ClF_2$, $C_2H_4Cl_2$, $C_2H_4ClF$, $C_3Cl_6F_2$, $C_3Cl_5F_3$, $C_3Cl_4F_4$, $C_3Cl_3F_5$, $C_3HCl_7$, $C_3HCl_6F$, $C_3HCl_5F_2$, $C_3HCl_4F_3$, $C_3HCl_3F_4$, $C_3HCl_2F_5$, $C_3H_2Cl_6$, $C_3H_2BrCl_5$, $C_3H_2Cl_5F$, $C_3H_2Cl_4F_2$, $C_3H_2Cl_3F_3$, $C_3H_2Cl_2F_4$, $C_3H_2ClF_5$, $C_3H_3Cl_5$, $C_3H_3Cl_4F$, $C_3H_3CO_3F_2$, $C_3H_3Cl_2F_3$, $C_3H_3ClF_4$, $C_3H_4Cl_4$, $C_4Cl_4Cl_4$, $C_4Cl_4Cl_6$, $C_4H_5Cl_5$, $C_4H_5Cl_4F$, and $C_5H_4C_{18}$.

Specific examples of fluorination reactions of saturated halogenated hydrocarbon compounds which may be carried out under the conditions described above using the catalysts of this invention include the conversion of $CH_2Cl_2$ to $CH_2F_2$, the conversion of $CHCl_3$ to a mixture of $CHCl_2F$, $CHClF_2$, and $CHF_3$, the conversion of $CH_3CHCl_2$ to a mixture of $CH_3CHClF$ and $CH_3CHF_2$, the conversion of $CH_2ClCH_2Cl$ to a mixture of $CH_3CHClF$ and $CH_3CHF_2$, the conversion of $CH_3CCl_3$ to a mixture of $CH_3CCl_2F$, $CH_3CClF_2$, and $CH_3CF_3$, the conversion of $CH_2ClCF_3$ to $CH_2FCF_3$, the conversion of $CHCl_2CF_3$ to a mixture of $CHClFCF_3$ and $CHF_2CF_3$, the conversion of $CHClFCF_3$ to $CHF_2CF_3$, the conversion of $CHBrFCF_3$ to $CHF_2CF_3$, the conversion of $CCl_3CF_2CCl_3$ to a mixture of $CCl_2FCF_2CClF_2$ and $CClF_2CF_2CClF_2$, the conversion of $CCl_3CH_2CCl_3$ to $CF_3CH_2CF_3$, the conversion of $CCl_3CH_2CHCl_2$ to a mixture of $CF_3CH_2CHF_2$, $CF_3CH=CHCl$, and $CF_3CH=CHF$, the conversion of $CF_3CCl_2CClF_2$ to a mixture of $CF_3CCl_2CF_3$, and $CF_3ClFCF_3$, the conversion of $CF_3CCl_2CF_3$ to $CF_3ClFCF_3$, and the conversion of a mixture comprising $CF_3CF_2CHCl_2$ and $CClF_2CF_2CHClF$ to a mixture of $CF_3CF_2CHClF$ and $CF_3CF_2CHF_2$.

Examples of unsaturated compounds of the formula $C_pH_eBr_fCl_gF_h$ and $C_iH_j$ which may be reacted with HF in the presence of the catalysts of this invention include $C_2Cl_4$, $C_2BrCl_3$, $C_2Cl_3F$, $C_2Cl_2F_2$, $C_2ClF_3$, $C_2F_4$, $C_2HCl_3$, $C_2HBrCl_2$, $C_2HCl_2F$, $C_2HClF_2$, $C_2HF_3$, $C_2H_2Cl_2$, $C_2H_2ClF$, $C_2H_2F_2$, $C_2H_3C_1$, $C_2H_3F$, $C_2H_4$, $C_3H_6$, $C_3H_5C_1$, $C_3H_4Cl_2$, $C_3H_3Cl_3$, $C_3H_2Cl_4$, $C_3HCl_5$, $C_3Cl_6$, $C_3Cl_5F$, $C_3Cl_4F_2$, $C_3Cl_3F_3$, $C_3Cl_2F_4$, $C_3ClF_5$, $C_3HF_5$, $C_3H_2F_4$, $C_3F_6$, $C_4Cl_8$, $C_4Cl_2F_6$, $C_4ClF_7$, $C_4H_2F_6$, and $C_4HClF_6$.

Specific examples of fluorination reactions of unsaturated halogenated hydrocarbon compounds which may be carried out using the catalysts of this invention include the conversion of $CHCl=CCl_2$ to a mixture of $CH_2ClCF_3$ and $CH_2FCF_3$, the conversion of $CCl_2=CCl_2$ to a mixture of $CHCl_2CF_3$, $CHClFCF_3$, and $CHF_2CF_3$, the conversion of $CCl_2=CH_2$ to a mixture of $CH_3CCl_2F$, $CH_3CClF_2$, and $CH_3CF_3$, the conversion of $CH_2=CHCl$ to a mixture of $CH_3CHClF$ and $CH_3CHF_2$, the conversion of $CF_2=CH_2$ to $CH_3CF_3$, the conversion of $CCl_2=CClCF_3$ to a mixture of $CF_3CHClCClF_2$, $CF_3CHClCF_3$, and/or $CF_3CCl=CF_2$, the conversion of $CF_3CF=CF_2$ to $CF_3CHFCF_3$, the conversion of $CF_3CH=CF_2$ to $CF_3CH_2CF_3$, and the conversion of $CF_3CH=CHF$ to $CF_3CH_2CHF_2$.

Further information on the production of pentafluoroethane is provided in U.S. patent application Ser. No. 60/405,223 [CL2109 US PRV] filed Aug. 22, 2002, and hereby incorporated by reference herein in its entirety.

Of note is a catalytic process for producing 1,1,1,2,2-pentafluoroethane (i.e., $CHF_2CF_3$ or HFC-125) by the fluorination of a haloethane of the formula $CHZ_2CZ_3$ where each Z is selected from the group consisting of F, Cl, and Br provided that no more than four of the Z are F. Preferred haloethanes of the formula $CHZ_2CZ_3$ include 2,2-dichloro-1,1,1-trifluoroethane (HCFC-123) and 1,2,2-trichloro-1,1-difluoroethane (HCFC-122). HFC-125 is produced by reacting the $CHZ_2CZ_3$ compounds with HF in the vapor phase in the presence of the catalysts of this invention. The reaction of the above pentahaloethanes with HF in the presence of the catalyst of the instant invention is preferably conducted at about 150° C. to about 400° C., more preferably from about 200° C. to about 380° C. The amount of HF fed to the reactor should be at least a stoichiometric amount based on the number of Cl or Br substituents in the $CHZ_2CZ_3$ starting material(s). In the case of fluorination of HCFC-123, the stoichiometric ratio of HF to HCFC-123 is 2:1. Preferred ratios of HF to $CHZ_2CZ_3$ starting material(s) are typically in the range of about the stoichiometric ratio to about 20:1. Preferred contact times are from 1 to 60 seconds. Oxygen in the form of air or co-fed with an inert diluent such as nitrogen, helium, or argon may be added along with the reactants or as a separate catalyst treatment, if desired.

Also of note is a catalytic process for producing 2-chloro-1,1,1,3,3,3-hexafluoropropane (i.e., $CF_3CHClCF_3$ or HCFC-226da) by the fluorination of a hexahalopropene of the formula $C_3Cl_{6-x}F_x$, wherein x equals 0 to 5. Preferred hexahalopropenes of the formula $C_3Cl_{6-x}F_x$ include 1,2,2-trichloro-3,3,3-trifluoro-1-propene (i.e., $CCl_2=CClCF_3$ or CFC-1213xa) and hexachloropropene (i.e., $CCl_2=CClCCl_3$). HCFC-226da is produced by reacting the above unsaturated compounds with HF in the vapor phase in the presence of the catalysts of this invention at temperatures from about 150° C. to about 400° C., preferably about 200° C. to about 350° C.

The amount of HF fed to the reactor should be at least a stoichiometric amount based on the number of Cl substituents in the $C_3Cl_{6-x}F_x$ starting material(s). In the case of fluorination of CFC-1213xa, the stoichiometric ratio of HF to CFC-1213xa is 3:1. Preferred ratios of HF to $C_3Cl_{6-x}F_x$ starting material(s) are typically in the range of about the stoichiometric ratio to about 25:1. Preferred contact times are from 1 to 60 seconds.

Mixtures of saturated halogenated hydrocarbon compounds or mixtures of unsaturated hydrocarbons and/or halogenated hydrocarbon compounds may also be used in the vapor phase fluorination reactions as well as mixtures comprising both unsaturated hydrocarbons and halogenated hydrocarbon compounds. Specific examples of mixtures of saturated halogenated hydrocarbon compounds and mixtures of unsaturated hydrocarbons and unsaturated halogenated hydrocarbon compounds that may be subjected to vapor phase fluorination using the catalysts of this invention include a mixture of $CH_2Cl_2$ and $CCl_2=CCl_2$, a mixture of $CCl_2FCClF_2$ and $CCl_3CF_3$, a mixture of $CCl_2=CCl_2$ and $CCl_2=CClCCl_3$, a mixture of $CH_2=CHCH_3$ and $CH_2=CClCH_3$, a mixture of $CH_2Cl_2$ and $CH_3CCl_3$, a mixture of $CHF_2CClF_2$ and $CHClFCF_3$, a mixture of $CHCl_2CCl_2CH_2Cl$ and $CCl_3CHClCH_2Cl$, a mixture of $CHCl_2CH_2CCl_3$ and $CCl_3CHClCH_2Cl$, a mixture of $CHCl_2CHClCCl_3$, $CCl_3CH_2CCl_3$, and $CCl_3CCl_2CH_2Cl$, a mixture of $CHCl_2CH_2CCl_3$ and $CCl_3CH_2CCl_3$, a mixture of and $CF_3CH_2CCl_2F$ and $CF_3CH=CCl_2$, and a mixture of $CF_3CH=CHCl$ and $CF_3CH=CCl_2$.

Chlorofluorination

Included in this invention is a process for increasing the fluorine content of a halogenated hydrocarbon compound or a hydrocarbon compound by reacting said compound with hydrogen fluoride (HF) and chlorine ($Cl_2$) in the vapor phase in the presence of a catalyst composition comprising at least one chromium-containing component selected from the group consisting of the crystalline cobalt-substituted alpha-chromium oxide described above and said cobalt-substituted alpha-chromium oxide which has been treated with a flu-orinating agent. The catalyst composition may optionally contain additional components such as another catalytically effective metal.

Halogenated hydrocarbon compounds suitable as starting materials for the chlorofluorination process of this invention may be saturated or unsaturated. Saturated halogenated hydrocarbon compounds suitable for the chlorofluorination processes of this invention include those of the general formula $C_nH_aBr_bCl_cF_d$, wherein n is an integer from 1 to 6, a is an integer from 0 to 12, b is an integer from 0 to 4, c is an integer from 0 to 13, d is an integer from 0 to 13, the sum of b, c and d is at least 1 and the sum of a, b, c, and d is equal to 2n+2, provided that a+b+c is at least 1. Preferred chlorofluorination processes include those involving said saturated starting materials where a is at least 1. Saturated hydrocarbon compounds suitable for chlorofluorination are those which have the formula $C_qH_r$ where q is an integer from 1 to 6 and r is 2q+2. Unsaturated halogenated hydrocarbon compounds suitable for the chlorofluorination processes of this invention include those of the general formula $C_pH_eBr_fCl_gF_h$, wherein p is an integer from 2 to 6, e is an integer from 0 to 10, f is an integer from 0 to 2, g is an integer from 0 to 12, h is an integer from 0 to 11, the sum of f, g and h is at least 1 and the sum of e, f, g, and h is equal to 2p. Unsaturated hydrocarbon compounds suitable for fluorination are those which have the formula $C_iH_j$ where i is an integer from 2 to 6 and j is 2i. The fluorine content of saturated compounds of the formula $C_nH_aBr_bCl_cF_d$ and $C_qH_r$ and/or unsaturated compounds of the formula $C_pH_eBr_fCl_gF_h$ and $C_iH_j$ may be increased by reacting said compounds with HF and $Cl_2$ in the vapor phase in the presence of a catalyst composition comprising at least one chromium-containing component selected from the group consisting of the crystalline cobalt-substituted alpha-chromium oxide described above and said cobalt-substituted alpha-chromium oxide which has been treated with a fluorinating agent. Such a process is referred to herein as a vapor phase chlorofluorination reaction.

The conditions of the vapor phase chlorofluorination reactions are similar to those described above for vapor phase fluorination reactions in terms of the temperature ranges, contact times, pressures, and mole ratios of HF to the halogenated hydrocarbon compounds. The amount of chlorine ($Cl_2$) fed to the reactor is based on whether the halogenated hydrocarbon compounds fed to the reactor is unsaturated and the number of hydrogens in $C_nH_aBr_bCl_cF_d$, $C_qH_r$, $C_pH_eBr_fCl_gF_h$, and $C_iH_j$ that are to be replaced by chlorine and fluorine. One mole of $Cl_2$ is required to saturate a carbon-carbon double bond and a mole of $Cl_2$ is required for every hydrogen to be replaced by chlorine or fluorine. A slight excess of chlorine over the stoichiometric amount may be necessary for practical reasons, but large excesses of chlorine will result in complete chlorofluorination of the products. The ratio of $Cl_2$ to halogenated carbon compound is typically from about 1:1 to about 10:1.

Specific examples of vapor phase chlorofluorination reactions of saturated halogenated hydrocarbon compounds of the general formula $C_nH_aBr_bCl_cF_d$ and saturated hydrocarbon compounds of the general formula $C_qH_r$ which may be carried out using the catalysts of this invention include the conversion of $C_2H_6$ to a mixture containing $CH_2ClCF_3$, the conversion of $CH_2ClCF_3$ to a mixture of $CHClFCF_3$ and $CHF_2CF_3$, the conversion of $CCl_3CH_2CH_2Cl$ to a mixture of $CF_3CCl_2CClF_2$, $CF_3CCl_2CF_3$, $CF_3CClFCClF_2$, and $CF_3CClFCF_3$, the conversion of $CCl_3CH_2CHCl_2$ to a mixture of $CF_3CCl_2CClF_2$, $CF_3CCl_2CF_3$, $CF_3CClFCClF_2$, and $CF_3CClFCF_3$, the conversion of $CCl_3CHClCH_2Cl$ to a mixture of $CF_3CCl_2CClF_2$, $CF_3CCl_2CF_3$, $CF_3CClFCClF_2$, and $CF_3CClFCF_3$, the conversion of $CHCl_2CCl_2CH_2Cl$ to a mixture of $CF_3CCl_2CClF_2$, $CF_3CCl_2CF_3$, $CF_3CClFCClF_2$, and $CF_3CClFCF_3$, the conversion of $CCl_3CH_2CH_2Cl$ to a mixture of $CF_3CCl_2CHF_2$, $CF_3CClFCHF_2$, $CF_3CClFCClF_2$, and $CF_3CCl_2CF_3$, and the conversion of $CCl_3CH_2CHCl_2$ to a mixture of $CF_3CCl_2CHF_2$, $CF_3CClFCHF_2$, $CF_3CClFCClF_2$, and $CF_3CCl_2CF_3$.

Specific examples of vapor phase chlorofluorination reactions of unsaturated halogenated hydrocarbon compounds of the general formula $C_pH_eBr_fCl_gF_h$ and unsaturated hydrocarbon compounds of the general formula $C_iH_j$ which may be carried out using the catalysts of this invention include the conversion of $C_2H_4$ to a mixture of $CCl_3CClF_2$, $CCl_2FCCl_2F$, $CClF_2CCl_2F$, $CCl_3CF_3$, $CF_3CCl_2F$, and $CClF_2CClF_2$, the conversion of $C_2Cl_4$ to a mixture of $CCl_3CClF_2$, $CCl_2FCCl_2F$, $CClF_2CCl_2F$, $CCl_3CF_3$, $CF_3CCl_2F$, and $CClF_2CClF_2$, and the conversion of $C_3H_6$ or $CF_3CCl=CCl_2$ to a mixture of $CF_3CCl_2CClF_2$, $CF_3CCl_2CF_3$, $CF_3CClFCClF_2$, and $CF_3CClFCF_3$.

Of note is a catalytic process for producing a mixture containing 2-chloro-1,1,1-trifluoroethane (i.e., $CH_2ClCF_3$ or HCFC-133a) by reaction of ethane with HF and $Cl_2$ in the vapor phase in the presence of the catalysts of this invention. The chlorofluorination of ethane is preferably conducted at about 150° C. to about 450° C., preferably from about 300° C. to about 400° C. The molar ratio of HF to ethane is preferably from about 3:1 to about 15:1 and the molar ratio of chlorine to ethane of from about 2:1 to 5:1. Preferred contacts times are from about 5 seconds to about 60 seconds. Oxygen in the form of air or co-fed with an inert diluent such as nitrogen, helium, or argon may be added along with the reactants or as a separate catalyst treatment, if desired.

Also of note is a catalytic process for producing a mixture of 1,2,2-trichloro-1,1,3,3,3-pentafluoropropane (i.e., $CClF_2CCl_2CF_3$ or CFC-215aa), 2,2-dichloro-1,1,1,3,3,3-hexafluoropropane (i.e., $CF_3CCl_2CF_3$ or CFC-216aa), 1,2-dichloro-1,1,3,3,3-hexafluoropropane (i.e., $CClF_2CClFCF_3$ or CFC-216ba), and 2-chloro-1,1,1,2,3,3,3-heptafluoropropane (i.e., $CF_3CClFCF_3$ or CFC-217ba), by the chlorofluorination of a hexahalopropene of the formula $C_3Cl_{6-x}F_x$, wherein x equals 0 to 4. Preferred hexahalopropenes of the formula $C_3Cl_{6-x}F_x$ include 1,2,2-trichloro-3,3,3-trifluoro-1-propene (i.e., $CCl_2=CClCF_3$ or CFC-1213xa) and hexachloropropene (i.e., $CCl_2=CClCCl_3$). The mixture of CFC-215aa, -216aa, -216ba, and -217ba is produced by reacting the above unsaturated compounds with $Cl_2$ and HF in the vapor phase in the presence of the catalysts of this invention at temperatures from about 150° C. to about 450° C., preferably about 250° C. to 400° C.

The amount of HF fed to the reactor should be at least a stoichiometric amount based on the number of Cl substitutents in the $C_3Cl_{6-x}F_x$ starting material(s) and the desired composition of the final product. In the case of chlorofluorination of CFC-1213xa to a mixture of chlorofluoropropanes having an average number of fluorine substituents of six, the stoichiometric ratio of HF to CFC-1213xa is 3:1. Preferred ratios of HF to $C_3Cl_{6-x}F_x$ starting material(s) are typically in the range of about the stoichiometric ratio to about 30:1, more preferably from about 8:1 to 25:1.

The amount of chlorine fed to the reactor should be at least a stoichiometric amount. Preferred molar ratios of $Cl_2$ to CFC-1213xa are from about 1:1 to about 5:1.

Preferred contact times are from about 5 seconds to about 60 seconds.

Further information on the chlorofluorination of CFC-1213xa is provided in U.S. patent application Ser. No. 60/405,222 [CL2108 US PRV] filed Aug. 22, 2002, and hereby incorporated by reference herein in its entirety.

Mixtures of saturated hydrocarbon compounds and saturated halogenated hydrocarbon compounds and mixtures of unsaturated hydrocarbon compounds and unsaturated halogenated hydrocarbon compounds as well as mixtures comprising both saturated and unsaturated compounds may be chlorofluorinated using the catalysts of the present invention. Specific examples of mixtures of saturated and unsaturated hydrocarbons and halogenated hydrocarbons that may be used include a mixture of $CCl_2=CCl_2$ and $CCl_2=CClCCl_3$, a mixture of $CHCl_2CCl_2CH_2Cl$ and $CCl_3CHClCH_2Cl$, a mixture of $CHCl_2CH_2CCl_3$ and $CCl_3CHClCH_2Cl$, a mixture of $CHCl_2CHClCCl_3$, $CCl_3CH_2CCl_3$, and $CCl_3CCl_2CH_2Cl$, a mixture of $CHF_2CH_2CF_3$ and $CHCl=CHCF_3$, and a mixture of $CH_2=CH_2$ and $CH_2=CHCH_3$.

Isomerization and Disproportionation

Included in this invention is a process for changing the fluorine distribution in a halogenated hydrocarbon compound by isomering said halogenated hydrocarbon compound in the presence of a catalyst composition comprising at least one chromium-containing component selected from the group consisting of the crystalline cobalt-substituted-chromium oxide described above and said cobalt-substituted alpha-chromium oxide which has been treated with a fluorinating agent.

Also included in this invention is a process for changing the fluorine distribution in a halogenated hydrocarbon compound by disproportionating said halogenated hydrocarbon compound in the vapor phase in the presence of a catalyst composition comprising at least one chromium-containing component selected from the group consisting of the crystalline cobalt-substituted alpha-chromium oxide described above and said cobalt-substituted alpha-chromium oxide which has been treated with a fluorinating agent.

Halogenated hydrocarbon compounds suitable as starting materials for the isomerization and disproportionation processes of this invention may be saturated or unsaturated. Saturated halogenated hydrocarbon compounds suitable for the isomerization and disproportionation processes of this invention include those of the general formula $C_nH_aBr_bCl_cF_d$, wherein n is an integer from 2 to 6, a is an integer from 0 to 12, b is an integer from 0 to 4, c is an integer from 0 to 13, d is an integer from 1 to 13, and the sum of a, b, c, and d is equal to 2n+2, provided that a+b+c is at least 1. Unsaturated halogenated hydrocarbon compounds suitable for the isomerization and disproportionation processes of this invention include those of the general formula $C_pH_eBr_fCl_gF_h$, wherein p is an integer from 2 to 6, e is an integer from 0 to 10, f is an integer from 0 to 2, g is an integer from 0 to 12, h is an integer from 1 to 11, and the sum of e, f, g, and h is equal to 2p, provided that the sum of e+f+g is at least 1.

In one embodiment of the present invention, the fluorine distribution of a halogenated hydrocarbon compound is changed by rearranging the H, Br, Cl, and F substituents in the molecule (typically to a thermodynamically preferred arrangement) while maintaining the same number of the H, Br, Cl, and F substituents, respectively. This process is referred to herein as isomerization.

In another embodiment of the present invention, the fluorine distribution of a halogenated hydrocarbon compound is changed by exchanging at least one F substituent of one molecule of the halogenated hydrocarbon starting material with at least one H, Br and/or Cl substituent of another molecule of the halogenated hydrocarbon starting material so as to result in the formation of one or more halogenated hydrocarbon compounds having a decreased fluorine content compared to the halogenated hydrocarbon starting material and one or more halogenated hydrocarbon compounds having an increased fluorine content compared to the halogenated hydrocarbon starting material. This process is referred to herein as disproportionation.

In another embodiment of the present invention, both isomerization and disproportionation reactions may occur simultaneously.

Whether carrying out isomerization, disproportionation or both isomerization and disproportionation, the fluorine distribution of saturated compounds of the formula $C_nH_aBr_b\text{-}Cl_cF_d$ and/or unsaturated compounds of the formula $C_pH_eBr_fCl_gF_h$ may be changed in the presence of a catalyst composition comprising at least one chromium-containing component selected from the group consisting of the crystalline cobalt-substituted alpha-chromium oxide described above and said cobalt-substituted alpha-chromium oxide which has been treated with a fluorinating agent.

The isomerization and disproportionation reactions are typically conducted at temperatures of from about 150° C. to 500° C., preferably from about 200° C. to about 400° C. The contact time in the reactor is typically from about 1 to about 120 seconds and preferably from about 5 to about 60 seconds. The isomerization and disproportionation reactions may be carried out in the presence of an inert gas such as helium, argon, or nitrogen though this is not preferred. The isomerization and disproportionation reactions may be carried out in the presence of HF and HCl, but this is not preferred.

Specific examples of vapor phase isomerization reactions which may be carried out using the catalysts of this invention include the conversion of $CClF_2CCl_2F$ to $CCl_3CF_3$, the conversion of $CClF_2CClF_2$ to $CF_3CCl_2F$, the conversion of $CHF_2CClF_2$ to $CF_3CHClF$, the conversion of $CHF_2CHF_2$ to $CF_3CH_2F$, the conversion of $CF_3CClFCClF_2$ to $CF_3CCl_2CF_3$, and the conversion of $CF_3CHFCHF_2$ to $CF_3CH_2CF_3$.

Specific examples of vapor phase disproportionation reactions which may be carried out using the catalysts of this invention include the conversion of $CClF_2CClF_2$ to a mixture of $CClF_2CCl_2F$, $CCl_3CF_3$, and $CF_3CClF_2$, and the conversion of $CHClFCF_3$ to a mixture of $CHCl_2CF_3$, and $CHF_2CF_3$.

Of note is a process for the conversion of a mixture of 2-chloro-1,1,2,2-tetrafluoroethane (i.e., $CHF_2CClF_2$ or HCFC-124a) and 2-chloro-1,1,1,2-tetrafluoroethane (i.e., $CF_3CHClF$ or HCFC-124) to a mixture comprising 2,2-dichloro-1,1,1-trifluoroethane (i.e., $CHCl_2CF_3$ or HCFC-123) and 1,1,1,2,2-pentafluoroethane (i.e., $CF_3CHF_2$ or HFC-125) in addition to unconverted starting materials. The mixture comprising HFC-125 and HCFC-123 may be obtained in the vapor phase by contacting a mixture of HCFC-124a and -124 over the catalysts of this invention optionally in the presence of a diluent selected from the group consisting of HF, HCl, nitrogen, helium, argon, and carbon dioxide. The disproportionation is preferably conducted at about 150° C. to about 400° C., more preferably about 250° C. to about 350° C. If used, the diluent gas, may be present in a molar ratio of diluent to haloethane of from about 1:1 to about 5:1. Preferred contact times are from about 10 seconds to about 60 seconds.

Dehydrofluorination

Included in this invention is a process for decreasing the fluorine content of a halogenated hydrocarbon compound by dehydrofluorinating said halogenated hydrocarbon compound in the presence of a catalyst composition comprising at least one chromium-containing component selected from the group consisting of the crystalline cobalt-substituted alpha-chromium oxide described above and said cobalt-substituted alpha-chromium oxide which has been treated with a fluorinating agent.

Halogenated hydrocarbon compounds suitable as starting materials for the dehydrofluorination process of this invention are typically saturated. Saturated halogenated hydrocarbon compounds suitable for the dehydrofluorination processes of this invention include those of the general formula $C_nH_aF_d$, wherein n is an integer from 2 to 6, a is an integer from 1 to 12, d is an integer from 1 to 13, and the sum of a and d is equal to 2n+2. The fluorine content of saturated compounds of the formula $C_nH_aF_d$ may be decreased in the presence of a catalyst composition comprising at least one chromium-containing component selected from the group consisting of the crystalline cobalt-substituted alpha-chromium oxide described above and said cobalt-substituted alpha-chromium oxide which has been treated with a fluorinating agent. This decrease in fluorine content is typically associated with removal of hydrogen fluoride (HF) from the molecule and is referred to herein as dehydrofluorination.

The dehydrofluorination reactions are typically conducted at temperatures of from about 200° C. to about 500° C., preferably from about 300° C. to about 450° C. The contact time in the reactor is typically from about 1 to about 360 seconds and preferably from about 5 to about 120 seconds. Carrying out the dehydrofluorination reactions in the presence of an inert gas such as helium, argon, or nitrogen promotes the dissociation of the fluorinated carbon compound, but this practice can also lead to difficulties in separation and is not preferred.

The product of dehydrofluorination reaction consists of HF and the unsaturated fluorinated carbon compound resulting from loss of HF from the starting material. Specific examples of vapor phase dehydrofluorination reactions which may be carried out using the catalysts of this invention include the conversion of $CH_3CHF_2$ to $CH_2=CHF$, the conversion of $CH_3CF_3$ to $CH_2=CF_2$, the conversion of $CF_3CH_2F$ to $CF_2=CHF$, the conversion of $CHF_2CH_2CF_3$ to $CHF=CHCF_3$, and the conversion of $CF_3CH_2CF_3$ to $CF_3CH=CF_2$.

Of note is a catalytic process for producing fluoroethene (i.e., $CH_2=CHF$ or vinyl fluoride) by the dehydrofluorination of a 1,1-difluoroethane (i.e., $CHF_2CH_3$ or HFC-152a). A mixture comprising vinyl fluoride and unconverted HFC-152a may be obtained in the vapor phase by contacting HFC-152a over the catalysts of this invention optionally in the presence of a diluent selected from the group consisting of HF, nitrogen, helium, argon, and carbon dioxide. The dehydrofluorination is preferably conducted at about 150° C. to about 400° C., more preferably about 250° C. to about 350° C. If used, the diluent gas, may be present in a molar ratio of diluent to haloethane of from about 1:1 to about 5:1. Preferred contact times are from about 10 seconds to about 60 seconds.

Chlorodefluorination

Included in this invention is a process for decreasing the fluorine content of a halogenated hydrocarbon compound by reacting said halogenated hydrocarbon compound with hydrogen chloride (HCl) in the vapor phase in the presence of a catalyst composition comprising at least one chromium-containing component selected from the group consisting of the crystalline cobalt-substituted alpha-chromium oxide described above and said cobalt-substituted alpha-chromium oxide which has been treated with a fluorinating agent.

Halogenated hydrocarbon compounds suitable as starting materials for the chlorodefluorination processes of this invention may be saturated or unsaturated. Saturated halogenated hydrocarbon compounds suitable for the chlorodefluorination processes of this invention include those of the general formula $C_nH_aCl_cF_d$, wherein n is an integer from 1 to 6, a is an integer from 0 to 12, c is an integer from 0 to 13, d is an integer from 1 to 13, and the sum of a, c and d is equal to 2n+2. Unsaturated halogenated hydrocarbon compounds suitable for the chlorodefluorination processes of this invention include those of the general formula $C_pH_eCl_gF_h$, wherein p is an integer from 2 to 6, e is an integer from 0 to 10, g is an integer from 0 to 12, h is an integer from 1 to 11, and the sum of e, g, and h is equal to 2p. The fluorine content of saturated compounds of the formula $C_nH_aCl_cF_d$ and/or unsaturated compounds of the formula $C_pH_eCl_gF_h$ may be decreased by reacting said compounds with HCl in the vapor phase in the presence of a catalyst composition comprising at least one chromium-containing component selected from the group consisting of the crystalline cobalt-substituted alpha-chromium oxide described above and said cobalt-substituted alpha-chromium oxide which has been treated with a fluorinating agent. Such a process is referred to herein as a vapor phase chlorodefluorination reaction. Chlorodefluorination is disclosed in U.S. Pat. No. 5,345,017 and U.S. Pat. No. 5,763,698 and the teachings of these two patents are hereby incorporated herein by reference.

The chlorodefluorination reactions are typically conducted at temperatures of from about 250° C. to 450° C., preferably from about 300° C. to about 400° C. The contact time in the reactor is typically from about 1 to about 120 seconds and preferably from about 5 to about 60 seconds. The reactions are most conveniently carried out at atmospheric or superatmospheric pressure.

Chlorodefluorinations involving saturated halogenated hydrocarbons are of particular note. The molar ratio of HCl to the saturated halogenated hydrocarbon compound is typically from about 1:1 to about 100:1, preferably from about 3:1 to about 50:1, and most preferably from about 4:1 to about 30:1. In general, with a given catalyst composition, the higher the temperature, the longer the contact time, and the greater the molar ratio of HCl to saturated halogenated hydrocarbon compound, the greater is the conversion to compounds having lower fluorine content. The above variables can be balanced, one against the other, so that the formation of chlorine-substituted products is maximized.

The product of chlorodefluorination reactions typically comprise unreacted HCl, HF, unconverted starting material, and saturated halogenated hydrocarbon compounds having a lower fluorine content than the starting material by virtue of the substitution of one or more fluorine substituents for chlorine. Specific examples of vapor phase chlorodefluorination reactions which may be carried out using the catalysts of this invention include the conversion of $CHF_3$ to a mixture of $CHCl_3$, $CHCl_2F$, and $CHClF_2$, the conversion of $CClF_2CClF_2$ to a mixture of $CCl_3CCl_3$, $CCl_3CCl_2F$, $CCl_3CClF_2$, $CCl_2FCCl_2F$, $CClF_2CCl_2F$, and $CCl_3CF_3$, the conversion of $CF_3CClF_2$ to a mixture of $CCl_3CCl_3$, $CCl_3CCl_2F$, $CCl_3CClF_2$, $CCl_2FCCl_2F$, $CClF_2CCl_2F$, $CCl_3CF_3$, $CClF_2CClF_2$, and $CF_3CCl_2F$, the conversion of $CF_3CCl_2CF_3$ to a mixture of $CF_3CCl_2CClF_2$, $CF_3CCl_2CCl_2F$, $CF_3CCl_2CCl_3$, and $CClF_2CCl_2CCl_3$, and the conversion of $CF_3CH_2CF_3$ to a mixture of $CCl_2=CHCF_3$, and $CCl_2=CClCF_3$.

Of note is a catalytic process for producing a mixture containing 1,1-dichloro-3,3,3-trifluoro-1-propene (i.e., $CCl_2=CHCF_3$ or HCFC-1223za) and 1,1,2-trichloro-3,3,3-trifluoro-1-propene (i.e., $CCl_2=CClCF_3$ or CFC-1213xa) by the chlorodefluorination of 1,1,1,3,3,3-hexafluoropropane (i.e., $CF_3CH_2CF_3$ or HFC-236fa) by reaction of HFC-236fa with HCl in the vapor phase in the presence of the catalysts of this invention. The reaction is preferably conducted from about 275° C. to about 450° C., more preferably about 300° C. to about 400° C. with a molar ratio of HCl to HFC-236fa of preferably from about 3:1 to about 20:1. Preferred contacts times are from about 1 second to about 40 seconds. Oxygen in the form of air or co-fed with an inert diluent such as nitrogen, helium, or argon may be added along with the reactants or as a separate catalyst treatment, if desired.

The reaction products obtained by the processes of this invention can be separated by conventional techniques, such as with combinations including, but not limited to, scrubbing, decantation, or distillation. Some of the products of the various embodiments of this invention may form one or more azeotropes with each other or with HF.

The processes of this invention can be carried out readily using well known chemical engineering practices.

Utility

Several of the reaction products obtained through use of the catalysts disclosed herein will have desired properties for direct commercial use. For example, $CH_2F_2$ (HFC-32), $CHF_2CF_3$ (HFC-125), $CHF_2CF_3$ (HFC-125), $CH_2FCHF_2$ (HFC-134), $CF_3CH_2CF_3$ (HFC-236fa), and $CF_3CH_2CHF_2$ (HFC-245fa) find application as refrigerants, $CH_2FCF_3$ (HFC-134a) and $CF_3CHFCF_3$ (HFC-227ea) find application as propellants, $CH_2FCHF_2$ (HFC-134) and $CF_3CH_2CHF_2$ (HFC-245fa) find application as blowing agents, and $CHF_2CF_3$ (HFC-125), $CF_3CH_2CF_3$ (HFC-236fa), and $CF_3CHFCF_3$ (HFC-227ea) find application as fire extinguishants.

Other reaction products obtained through the use of this invention are used as chemical intermediates to make useful products. For example, $CCl_3CF_3$ (CFC-113a) can be used to prepare CFC-114a which can then be converted to $CH_2FCF_3$ (HFC-134a) by hydrodechlorination. Similarly, $CF_3CCl_2CF_3$ (CFC-216aa) can be used to prepare $CF_3CH_2CF_3$ (HFC-236fa) by hydrodechlorination and $CF_3CCl=CF_2$ (CFC-1215zc) can be used to prepare $CF_3CH_2CHF_2$ (HFC-245fa) by hydrogenation.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

Catalyst Characterization

Energy Dispersive Spectroscopy (EDS) and Transmission Electron Microscopy (TEM)

In these studies, the crystallites were analyzed using a Philips CM-20 high-resolution transmission electron microscope operated at an accelerating voltage of 200 kV and configured with an Oxford windowless EDS system with a Si(Li) elemental detector. In the EDS analyses, electron-transparent thin sections of samples were used to minimize sample thickness effects such as fluorescence. Also, due to the similarity of their atomic masses, the X-ray absorption cross-sections for Cr, Co, and Ni were assumed to be the same (see the discussion by Zaluzec on pages 121 to 167 in *Introduction to Analytical Electron Microscopy* edited by J. J. Hren, J. I. Goldstein, and D. C. Joy (Plenum Press, New York, 1979). The presence of copper in the EDS of FIGS. 1, 2, and 3 is due to the TEM grid and background in the microscope.

X-Ray Absorption Spectroscopy (XAS) and X-Ray Powder Diffraction (XRD)

XRD data were obtained and analyzed according to methods described by Warren in *X-Ray Diffraction* (Addison-Wesley, Reading, Mass., 1969). XAS data were obtained at beamline 5BMD, DND-CAT, of the Advanced Photon Source, Argonne National Laboratory. XAS data were obtained and analyzed using the methods described in Koningsberger and Prins in *X-ray Absorption: Principles, Applications, Techniques of EXAFS, SEXAFS and XANES* (John Wiley & Sons, New York, 1988). Spectra were obtained for the K edges of Cr, Co, and Ni. Cr edges were obtained in transmission geometry, while Co and Ni edges were obtained in fluorescence mode, due to their low concentrations.

The data in Table 2 represent bulk averages over all Co atoms. Coordination numbers are extracted from the radial distribution function obtained by Fourier transform of the extended x-ray absorption fine structure (EXAFS) region of the Co spectra. Oxidation states were obtained by fitting of sample near edge Co spectra to those of standards with known oxidation states.

Use of the Advanced Photon Source for acquiring XRD and XAS data was supported by the U.S. Department of Energy, Office of Basic Energy Sciences, under Contract No. W-31-109-Eng-38.

Catalyst Preparations

Comparative Preparation Example 1

Preparation of 100% Chromium Catalyst (400° C.)

A solution of 400 g $Cr(NO_3)_3[9(H_2O)]$ (1.0 mole) in 1000 mL of deionized water was treated dropwise with 477 mL of 7.4M aqueous ammonia raising the pH to about 8.5. The slurry was stirred at room temperature overnight. After re-adjusting the pH to 8.5 with ammonia, the mixture was poured into evaporating dishes and dried in air at 120° C. The resulting solid was then calcined in air at 400° C. for 24 hours.

The 100% chromium oxide was studied by TEM and EDS. The product consisted of uniform crystallites of $\alpha\text{-}Cr_2O_3$ with a narrow size range of about 20 nm. EDS indicated the presence of chromium and oxygen with no contaminants.

Preparation Example 2

Preparation of 99% Chromium/1% Cobalt Catalyst (400° C.)

A solution of 792.29 g $Cr(NO_3)_3[9(H_2O)]$ (1.98 moles) and 5.82 g $Co(NO_3)_2[6(H_2O)]$ (0.0200 mole) was prepared in 2000 mL of deionized water. The solution was treated dropwise with 955 mL of 7.4M aqueous ammonia which raised the pH to about 8.5. The slurry was stirred at room temperature overnight. The pH was adjusted to 8.5 the following day. The solid was then collected using two fritted funnels; the resulting solid in each funnel was washed with 15–20 liters of deionized water. The solids were dried in air at 120° C. for 24 hours and then calcined in air at 400° C. for 24 hours.

Analysis of the sample by TEM and EDS indicated the presence of $\alpha\text{-}Cr_2O_3$ crystallites in the size range of 20–40 nm. Cobalt was present in the chromium oxide lattice.

Preparation Example 3

Preparation of 98% Chromium/2% Cobalt Catalyst (400° C.)

A solution of 784.30 g $Cr(NO_3)_3[9(H_2O)]$ (1.96 moles) and 11.64 g $Co(NO_3)_2[6(H_2O)]$ (0.040 mole) was prepared in 2000 mL of deionized water. The solution was treated dropwise with 950 mL of 7.4M aqueous ammonia which raised the pH from about 1.8 to about 8.5. The slurry was stirred at room temperature overnight and then evaporated to dryness in air at 110–120° C. for 48 hours. The dried catalyst was divided in half. One half was calcined in air at 400° C. for 24 hours.

The Cr/Co oxide was studied by TEM and EDS. The oxides consisted of crystallites in the range of 20–40 nm. The EDS spectra indicated a uniform distribution of cobalt throughout the $\alpha\text{-}Cr_2O_3$ structure. Analysis of the sample by XRD and XAS confirmed that the crystallites had an $\alpha\text{-}Cr_2O_3$ structure and that the average oxidation state of cobalt was 2.94. The amount of cobalt incorporation in the $\alpha\text{-}Cr_2O_3$ lattice was in the range of 1.7 to 2.0 atom %.

Preparation Example 4

Preparation of 98% Chromium/2% Cobalt Catalyst (900° C.)

The other half of the dried catalyst prepared in Preparation Example 3 was calcined in air at 900° C. for 24 hours.

Preparation Example 5

Preparation of 98% Chromium/2% Cobalt Catalyst (400° C.)

A solution of 784.29 g $Cr(NO_3)_3[9(H_2O)]$ (1.96 moles) and 11.64 g $Co(NO_3)_2[6(H_2O)]$ (0.040 mole) was prepared in 2000 mL of deionized water. The solution was treated dropwise with 950 mL of 7.4M aqueous ammonia until the pH reached about 8.5. The slurry was stirred at room temperature for 24 hours while maintaining the pH at 8.5. The slurry was then evaporated to dryness in air at 110–120° C. with heating at 120° C. continuing over the weekend. The dried catalyst was then calcined in air at 400° C. for 24 hours.

Preparation Example 6

Preparation of 98% Chromium/2% Cobalt Catalyst (550° C.)

A solution of 1,010 g $Cr(NO_3)_3[9(H_2O)]$ (2.52 moles) and 14.6 g $Co(NO_3)_2[6(H_2O)]$ (0.050 mole) was prepared in 1000 mL of deionized water. The green solution was evaporated at a temperature of about 100° C. until a thick, black precipitate formed. The solid was dried at 300–325° C. on a hot plate. The solid was then transferred to a porcelain dish and calcined in a furnace at 550° C. for 20 hours.

Analysis of the sample by TEM and EDS indicated the presence of crystals of the cobalt-substituted $\alpha$-$Cr_2O_3$ with only minor increase in particle size due to the higher calcination temperature. The particle size of the spinel phase increased to about 20 to 50 nm compared with 10 to 30 nm observed in the sample calcined at 400° C.

Preparation Example 7

Preparation of 98% Chromium/2% Cobalt Catalyst (400° C.)

$Cr(NO_3)_3[9(H_2O)]$ (50.5 g, 0.126 mole) and $Co(NO_3)_2[6(H_2O)]$ (0.73 g, 0.00251 mole) were weighed into a porcelain crucible and melted together with stirring in the open air. The mixture was heated to decomposition and then calcined in a furnace at 400° C. for 24 hours.

Analysis of the sample by TEM and EDS indicated the presence of 100–150 nm crystals of cobalt-substituted $\alpha$-$Cr_2O_3$ as well as a relatively large quantity of the spinel phase having a particle size of about 10 to 30 nm.

In a manner similar to that above, cobalt/chromium oxide compositions having the bulk composition 0.5 atom % cobalt/99.5 atom % chromium, 1.0 atom % cobalt/99 atom % chromium, 3 atom % cobalt/97 atom % chromium, and 4 atom % cobalt/96 atom % chromium were prepared and calcined at 400° C.

Thermogravimetric analysis of these five cobalt/chromium compositions indicated that calcination at 400° C. resulted in incomplete decomposition of the nitrate precursors. The samples of the five compositions were re-calcined at 550° C. for 12 hours.

Analysis of these samples by XAS indicated the average oxidation state of cobalt was +3.0 to +3.2. The sample containing nominally 0.5 atom % cobalt was too dilute in cobalt for XAS work. The average oxidation state of chromium was +3.2; a phase containing a small amount of $Cr^{+6}$ was also present. XRD and XAS data indicated the local structure around cobalt was consistent with its presence in an $\alpha$-$Cr_2O_3$ lattice. A second phase is also present with very small particle size which is believed to be $CrCoO_3$.

Preparation Example 8

Preparation of 97.8% Chromium/2.2% Cobalt Catalyst (550° C.)

$Cr(NO_3)_3[9(H_2O)]$ (50.33 g, 0.126 mole) and $Co(NO_3)_2[6(H_2O)]$ (0.82 g, 0.00282 mole) were weighed into a porcelain crucible and melted together with stirring in the open air. The mixture was heated to decomposition and then calcined in a furnace at 550° C. for 12 hours.

In a manner similar to that above, cobalt/chromium oxide compositions having the bulk composition 2.4 atom % cobalt/97.6 atom % chromium and 2.7 atom % cobalt/97.3 atom % chromium were prepared and calcined at 550° C.

Analysis of these three samples by XAS indicated the average oxidation state of cobalt was +3.1 to +3.2. The average oxidation state of chromium was +3.13 to +3.20 with a phase containing a small amount of $Cr^{+6}$ also present. XRD and XAS data indicated the local structure around cobalt was consistent with its presence in an $\alpha$-$Cr_2O_3$ lattice. A second phase is also present with very small particle size which is believed to be $CrCoO_3$.

Preparation Example 9

Preparation of 98% Chromium/2% Cobalt Catalyst (550° C.)

A solution of 1,010 g $Cr(NO_3)_3[9(H_2O)]$ (2.52 moles) and 14.6 g $Co(NO_3)_2[6(H_2O)]$ (0.0502 mole) was prepared in 1500 mL of deionized water. The solution was treated with 500 mL of 29 weight percent aqueous ammonia with mixing provided by a mechanical stirrer. The mixture was stirred for two hours and the pH stabilized at 6.0. The mixture was transferred to a large, ceramic dish. Water was driven off by heating. After most of the water had evaporated, the sample was heated to 250–300° C. on a hot plate. The resulting solid was then transferred to a porcelain dish and calcined in a furnace at 550° C. for 20 hours.

Analysis of the sample by TEM and EDS indicated that formation of the spinel phase was minimal by the precipitation technique. About 90% of the cobalt-substituted $\alpha$-$Cr_2O_3$ phase consisted of crystallites in the size range of 20–40 nm with the remaining 10% being very large crystallites in the size range of 200–400 nm.

Preparation Example 10

Preparation of 97% Chromium/3% Cobalt Catalyst (unwashed, 400° C.)

A solution of 776.29 g $Cr(NO_3)_3[9(H_2O)]$ (1.94 moles) and 17.46 g $Co(NO_3)_2[6(H_2O)]$ (0.060 mole) was prepared in 2000 mL of deionized water. The solution was treated dropwise with 950 mL of 7.4M aqueous ammonia until the pH reached about 8.5. The slurry was stirred at room temperature for 24 hours and then evaporated to dryness in air at 110–120° C. The dried catalyst was ground to a powder and then calcined in air at 400° C. for 24 hours. The surface area of the calcined product was 30.5 $m^2/g$.

Preparation Example 11

Preparation of 97% Chromium/3% Cobalt Catalyst (washed; 400° C.)

A solution of 776.29 g $Cr(NO_3)_3[9(H_2O)]$ (1.94 moles) and 17.46 g $Co(NO_3)_2[6(H_2O)]$ (0.060 mole) was prepared in 2000 mL of deionized water. The solution was treated dropwise with 955 mL of 7.4M aqueous ammonia which raised the pH to about 8.5. The slurry was stirred at room temperature overnight and the pH adjusted to 8.5 the following day. The solid was collected in two 3 L fritted funnels and each portion washed with 15–20 L of deionized water. The washed solid was then evaporated to dryness in air at 120° C. for 24 hours and then calcined in air at 400° C. for 24 hours. The surface area of the calcined product was 17.8 $m^2/g$.

The Cr/Co oxide was studied by TEM and EDS. The $\alpha$-$Cr_2O_3$ phase consisted of crystallites in the range of 100 nm and the EDS spectrum indicated the presence of cobalt substituted into the lattice. This sample also contained a second phase consisting of crystallites in the size range of 10 nm. The EDS spectrum indicated that this phase contained comparable amounts of cobalt and chromium and was likely a spinel phase.

Preparation Example 12

Preparation of 95% Chromium/5% Cobalt Catalyst (900° C.)

A solution of 380.14 g $Cr(NO_3)_3[9(H_2O)]$ (0.95 moles) and 14.55 g $Co(NO_3)_2[6(H_2O)]$ (0.050 mole) was prepared in 1000 mL of deionized water. The solution was treated dropwise with 450 mL of 7.4 M aqueous ammonia as the pH increased from about 1.7 to 8.4. The slurry was stirred at room temperature overnight and then evaporated to dryness in air at 120° C. and held at that temperature overnight. The dried catalyst was ground to a powder and then calcined in air at 900° C. for 20 hours.

Preparation Example 13

Preparation of 95% Chromium/5% Cobalt Catalyst (400° C.)

A solution of 760.28 g $Cr(NO_3)_3[9(H_2O)]$ (1.90 moles) and 29.10 g $Co(NO_3)_2[6(H_2O)]$ (0.10 mole) was prepared in 2000 mL of deionized water. The solution was treated dropwise with 950 mL of 7.4M aqueous ammonia which raised the pH to about 8.5. The slurry was stirred at room temperature overnight and then evaporated to dryness in air at 110–120° C. for 48 hours. The dried catalyst was divided in half. One half was calcined in air at 400° C. for 24 hours. The surface area of the calcined product was 33.6 m²/g.

The Cr/Co 95/5 oxide was studied by TEM and EDS. The $\alpha$-$Cr_2O_3$ phase consisted of crystallites in the range of 50 nm and the EDS spectrum indicated the presence of cobalt substituted into the lattice. This sample also contained small crystallites of a spinel phase. Analysis of the sample by XRD and XAS confirmed that the crystallites had an $\alpha$-$Cr_2O_3$ structure and that the average oxidation state of cobalt was 2.84. The amount of cobalt incorporation in the $\alpha$-$Cr_2O_3$ lattice was in the range of 3.8 to 4.4 atom %.

Preparation Example 14

Preparation of 95% Chromium/5% Cobalt Catalyst (900° C.)

The other half of the dried catalyst prepared in PREPARATION EXAMPLE 13 was calcined in air at 900° C. for 24 hours.

Preparation Example 15

Preparation of 95% Chromium/5% Cobalt Catalyst 1.5 eq. excess $NH_4NO_3$, 400° C.

A solution of 760.28 g $Cr(NO_3)_3[9(H_2O)]$ (1.90 moles) and 29.10 g $Co(NO_3)_2[6(H_2O)]$ (0.10 mole) was prepared in 2000 mL of deionized water. The solution was treated dropwise with 950 mL of 7.4M aqueous ammonia; the pH reached 8.5. The slurry was stirred at room temperature for 24 hours and then treated with a solution of 240.12 g $NH_4NO_3$ (3.0 moles). After stirring at room temperature for 2 hours, the mixture was evaporated to dryness in air at 120° C. and held at that temperature over the weekend. The dried catalyst was ground to a powder with a mortar and pestle and then calcined in air at 400° C. for 24 hours. The surface area of the calcined product was 36.5 m²/g.

Preparation Example 16

Preparation of 90% Chromium/10% Cobalt Catalyst (washed; 400° C.)

A solution of 720.27 g $Cr(NO_3)_3[9(H_2O)]$ (1.80 moles) and 58.21 g $Co(NO_3)_2[6(H_2O)]$ (0.20 mole) was prepared in 2000 mL of deionized water. The solution was treated dropwise with 955 mL of 7.4M aqueous ammonia which raised the pH from about 2.1 to about 8.5. The slurry was stirred at room temperature overnight. The following day, the pH was the increased from 8.05 to 8.5 by addition of aqueous ammonia. The solid was collected in two 3 L fritted funnels and each portion washed with 15–20 L of deionized water. The washed solid was then evaporated to dryness in air at 120° C. for 24 hours. The dried catalyst was then calcined in air at 400° C. for 24 hours.

The Cr/Co 90/10 oxide was studied by TEM and EDS. The sample consisted of two phases. The $\alpha$-$Cr_2O_3$ phase consisted of crystallites in the range of 100 nm and the EDS spectrum indicated the presence of cobalt in the lattice. This sample also contained a relatively large amount of a spinel-like phase in the form of 10 nm crystallites. Analysis of the sample by XRD and XAS indicated the sample was mostly an $\alpha$-$Cr_2O_3$ structure and that the average oxidation state of cobalt was 2.63. The amount of cobalt incorporation in the $\alpha$-$Cr_2O_3$ lattice was in the range of 4.5 to 5.9 atom %.

Preparation Example 17

Preparation of 90% Chromium/10% Cobalt Catalyst 3.3 eq. excess $NH_4NO_3$; 400° C.

A solution of 72.03 g $Cr(NO_3)_3[9(H_2O)]$ (0.18 mole) and 5.82 g $Co(NO_3)_2[6(H_2O)]$ (0.020 mole) was prepared in 200 mL of deionized water. The solution was brought to pH 8.5 treatment with 7.4M aqueous ammonia. The slurry was stirred at room temperature for 24 hours. The mixture was then treated with a solution of 48.02 g of $NH_4NO_3$ (0.60 mole) dissolved in 100 mL of water. The slurry was stirred for one hour and then dried at 120° C. in air for about 90 hours. The dried solid was crushed to a powder and then placed in covered dish and calcined at 400° C. for 24 hours in air.

Analysis of the sample by XRD indicated the $\alpha$-$Cr_2O_3$ structure of the primary crystalline phase had a lattice contraction consistent with the presence of $Co^{+3}$ substitution for $Cr^{+3}$. The size range of the crystallites was about half of that observed in Preparation Example 16.

Preparation Example 18

Preparation of 90% Chromium/10% Cobalt Catalyst 6.7 eq. excess $NH_4NO_3$; 400° C.

The oxide preparation above was repeated except that the mixture of chromium/cobalt oxide/hydroxides was treated with a solution of 96.05 g of $NH_4(NO_3)$ (1.2 moles) dissolved in 200 mL of water.

Analysis of the sample by XRD indicated the $\alpha$-$Cr_2O_3$ structure of the primary crystalline phase had a lattice contraction consistent with the presence of $Co^{+3}$ substitution for $Cr^{+3}$. The size range of the crystallites was about half of that observed in Preparation Example 16.

General Procedure for Fluorocarbon Product Analysis

The following general procedure is illustrative of the method used for analyzing the products of fluorocarbon reactions. Part of the total reactor effluent was sampled on-line for organic product analysis using a gas chromatograph equipped a mass selective detector (GC-MS). The gas chromatography was accomplished with a 20 ft. (6.1 m) long×⅛ in. (0.32 cm) diameter tubing containing Krytox® perfluorinated polyether on an inert carbon support. The helium flow was 30 mL/min. Gas chromatographic conditions were 60° C. for an initial hold period of three minutes followed by temperature programming to 200° C. at a rate of 6° C./minute.

The bulk of the reactor effluent containing organic products and also inorganic acids such as HCl and HF was treated with aqueous caustic prior to disposal.

All vapor reactions were conducted at a nominal pressure of one atmosphere.

Legend

| | |
|---|---|
| 12 is $CCl_2F_2$ | 13 is $CClF_3$ |
| 21 is $CHCl_2F$ | 22 is $CHClF_2$ |
| 23 is $CHF_3$ | 32 is $CH_2F_2$ |
| 112 is $CCl_2FCCl_2F$ | 112a is $CCl_3CClF_2$ |
| 113 is $CCl_2FCClF_2$ | 113a is $CCl_3CF_3$ |
| 114 is $CClF_2CClF_2$ | 114a is $CF_3CCl_2F$ |
| 115 is $CF_3CClF_2$ | 116 is $CF_3CF_3$ |
| 122 is $CHCl_2CClF_2$ | 123 is $CHCl_2CF_3$ |
| 123a is $CHClFCClF_2$ | 123b is $CHF_2CCl_2F$ |
| 124 is $CHClFCF_3$ | 124a is $CHF_2CClF_2$ |
| 125 is $CHF_2CF_3$ | 132a is $CHF_2CHCl_2$ |
| 133a is $CH_2ClCF_3$ | 134 is $CHF_2CHF_2$ |
| 134a is $CH_2FCF_3$ | 143a is $CH_3CF_3$ |
| 152a is $CH_3CHF_2$ | 1110 is $CCl_2=CCl_2$ |
| 1111 is $CClF=CCl_2$ | 1112a is $CF_2=CCl_2$ |
| 1113 is $CF_2=CClF$ | 1120 is $CHCl=CCl_2$ |
| 1122 is $CHCl=CF_2$ | 1130 is $C_2H_2Cl_2$ |
| 1140 is $CH_2=CHCl$ | 1141 is $CHF=CH_2$ |
| 214 is $C_3Cl_4F_4$ | 214ab is $CF_3CCl_2CCl_2F$ |
| 215aa is $CF_3CCl_2CClF_2$ | 215bb is $CF_3CClFCClF_3$ |
| 216aa is $CF_3CCl_2CF_3$ | 216ba is $CClF_2CClFCF_3$ |
| 216ca is $CClF_2CF_2CClF_2$ | 216cb is $CCl_2FCF_2CF_3$ |
| 217ba is $CF_3CClFCF_3$ | 217ca is $CClF_2CF_2CF_3$ |
| 218 is $CF_3CF_2CF_3$ | 224aa is $CF_3CCl_2CHClF$ |
| 224ba is $CF_3CClFCHCl_2$ | 224ca is $CClF_2CF_2CHCl_2$ |
| 225ba is $CHClFCClFCF_3$ | 225ca is $CF_3CF_2CHCl_2$ |
| 225cb is $CClF_2CF_2CHClF$ | 225da is $CF_3CHClCClF_2$ |
| 226ca is $CF_3CF_2CHClF$ | 226da is $CF_3CHClCF_3$ |
| 227ca is $CF_3CF_2CHF_2$ | 227ea is $CF_3CHFCF_3$ |
| 235bb is $CF_3CClFCH_2F$ | 235da is $CF_3CHClCHF_2$ |
| 235fa is $CF_3CH_2CClF_2$ | 236fa is $CF_3CH_2CF_3$ |
| 244eb is $CF_3CHFCH_2Cl$ | 245eb is $CF_3CHFCH_2F$ |
| 245fa is $CF_3CH_2CHF_2$ | 253fb is $CF_3CH_2CH_2Cl$ |
| 254fb is $CF_3CH_2CH_2F$ | 263fb is $CF_3CH_2CH_3$ |
| 1213xa is $CF_3CCl=CCl_2$ | 1214 is $C_3Cl_2F_4$ |
| 1215 is $C_3ClF_5$ | 1215xc is $CF_3CCl=CF_2$ |
| 1222 is $C_3HCl_3F_2$ | 1223 is $C_3HCl_2F_3$ |
| 1223za is $CCl_2=CHCF_3$ | 1224 is $C_3HClF_4$ |
| 1225zc is $CF_3CH=CF_2$ | 1234yf is $CH_2=CFCF_3$ |
| 1234ze is E- and Z-$CHF=CHCF_3$ | 1316 is $C_4Cl_2F_6$ |
| 1326 is $C_4HClF_6$ | HFP is $CF_2=CFCF_3$ |
| TFE is $CF_2=CF_2$ | |

Example 19

Fluorination of $CF_3CHCl_2$

Cobalt-substituted chromium oxide (Cr/Co 95/5, 29.04 g, 20 mL, −12 to +20 mesh (1.68 to 0.84 mm)), prepared as described in Preparation Example 15 was placed in a ⅝" (1.58 cm) diameter Inconel™ nickel alloy reactor tube heated in a fluidized sand bath. The catalyst was heated from 77° C. to 175° C. in a flow of nitrogen (25 cc/min, $4.2\times10^{-7}$ m³/s) over the course of about 1.2 hours. HF and nitrogen were then co-fed to the reactor at a flow rate of 50 cc/min ($8.3\times10^{-7}$ m³/s) each. After 1.5 hours, the nitrogen flow was decreased to 20 cc/min ($3.3\times10^{-7}$ m³/s) and the HF flow increased to 80 cc/min ($1.3\times10^{-6}$ m³/s). The reactor temperature was gradually increased to 413° C. during a 5 hour period and maintained at 413° C. for an additional 0.6 hour. At the end of this period, the HF flow was stopped and the reactor cooled to 300° C. under 20 sccm ($3.3\times10^{-7}$ m³/s) nitrogen flow.

The catalyst prepared as above was placed in the reactor, purged with nitrogen and HF at 300° C. HF and HCFC-123 vapor were co-fed to the reactor in molar ratio of 6:1 at a contact time of 30 seconds. Analysis of the reactor effluent by GC-MS is given below.

| Component | Mole % |
|---|---|
| HFC-125 | 26.7 |
| HCFC-124 | 49.2 |
| HCFC-124a | 0.2 |
| CFC-114a | 1.4 |
| HCFC-123 | 22.1 |

Other products included CFC-113a, CFC-113, CFC-115.

Example 20

Fluorination of $CF_3CHClF$

Cobalt-substituted chromium oxide (Cr/Co 90/10, 6.75 g, 4 mL, 12–20 mesh, (1.68 to 0.84 mm)), prepared as described in Preparation Example 16 was placed in a ½" (1.27 cm) diameter Inconel™ nickel alloy reactor tube heated in a furnace. The catalyst was heated from 200° C. to 400° C. in a flow of nitrogen (50 cc/min, $8.3\times10^{-7}$ m³/s) over the course of about 25 minutes, and then the temperature was lowered to 300° C. while maintaining the nitrogen flow for an additional 80 minutes. The flow of nitrogen was reduced to 35 cc/min ($5.8\times10^{-7}$ m³/s) and HF was then admitted to the reactor at a flow rate of 12 cc/min ($2.0\times10^{-7}$ m³/s). After 35 minutes, the temperature was raised to 325° C. After 60 minutes it was raised to 350° C. After 60 minutes it was raised to 375° C. After 90 minutes it was raised to 400° C. After 30 minutes it was raised to 425° C. After 20 minutes, the flow of nitrogen was reduced to 15 cc/min ($2.5\times10^{-7}$ m³% s) and the flow of HF was increased to 28 cc/min ($4.7\times10^{-7}$ m³/s). After 20 minutes, the flow of nitrogen was reduced to 5 cc/min ($8.3\times10^{-8}$ m³% s) and the flow of HF was increased to 36 cc/min ($6.0\times10^{-7}$ m³/s). After 20 minutes, the flow of nitrogen was shut off and the flow of HF was increased to 40 cc/min ($6.7\times10^{-7}$ m³/s), and this condition was maintained for 120 minutes. The reactor temperature was adjusted to 350° C. and HF and HCFC-124 vapor were fed to the reactor in molar ratio of 2:1 at a contact time of 3.3 seconds. Analysis of the reactor effluent by GC-MS is given below.

| Component | Mole % |
|---|---|
| HFC-125 | 19.1 |
| CFC-115 | 48 ppm |

-continued

| Component | Mole % |
|---|---|
| HCFC-124 | 77.5 |
| HCFC-124a | 0.4 |
| HCFC-123 | 3.0 |

Example 21

Fluorination of $CF_3CHClF$

Cobalt-substituted chromium oxide which had been pre-treated with excess $NH_4NO_3$ (Cr/Co 90/10, 5.66 g, 4 mL, 12–20 mesh, (1.68 to 0.84 mm)), prepared as described in PREPARATION EXAMPLE 18, was placed in a ½" (1.27 cm) diameter Inconel™ nickel alloy reactor tube heated in a furnace. The catalyst was heated from 200° C. to 400° C. in a flow of nitrogen (50 cc/min, $8.3 \times 10^{-7}$ m³/s) over the course of about 25 minutes, and then the temperature was lowered to 300° C. while maintaining the nitrogen flow for an additional 80 minutes. The flow of nitrogen was reduced to 35 cc/min ($5.8 \times 10^{-7}$ m³/s) and HF was then admitted to the reactor at a flow rate of 12 cc/min ($2.0 \times 10^{-7}$ m³/s). After 35 minutes, the temperature was raised to 325° C. After 60 minutes it was raised to 350° C. After 60 minutes it was raised to 375° C. After 90 minutes it was raised to 400° C. After 30 minutes it was raised to 425° C. After 20 minutes, the flow of nitrogen was reduced to 15 cc/min ($2.5 \times 10^{-7}$ m³/s) and the flow of HF was increased to 28 cc/min ($4.7 \times 10^{-7}$ m³/s). After 20 minutes, the flow of nitrogen was reduced to 5 cc/min ($8.3 \times 10^{-8}$ m³/s) and the flow of HF was increased to 36 cc/min ($6.0 \times 10^{-7}$ m³). After 20 minutes, the flow of nitrogen was shut off and the flow of HF was increased to 40 cc/min ($6.7 \times 10^{-7}$ m³/s), and this condition was maintained for 120 minutes. The reactor temperature was adjusted to 350° C. and HF and HCFC-124 vapor were fed to the reactor in molar ratio of 2:1 at a contact time of 3.3 seconds. Analysis of the reactor effluent by GC-MS is given below.

| Component | Mole % |
|---|---|
| HFC-125 | 62.0 |
| CFC-115 | 200 ppm |
| HCFC-124 | 23.3 |
| HCFC-124a | 0.2 |
| HCFC-133a | 0.3 |
| FCFC-114a | 0.1 |
| HCFC-123 | 14.0 |
| FCFC-113 | 0.1 |

Example 22

Fluorination of $CCl_2=CCl_2$

Cobalt-substituted chromium oxide (Cr/Co 90/10, 32.26 g, 20 mL,–12 to +20 mesh, (1.68 to 0.84 mm)), prepared as described in Preparation Example 16 was placed in a ⅝" (1.58 cm) diameter Inconel™ nickel alloy reactor tube heated in a fluidized sand bath. The catalyst was heated from 50° C. to 246° C. in a flow of nitrogen (50 cc/min, $8.3 \times 10^{-7}$ m³/s) over the course of about 1.6 hours. The catalyst was purged with 20 cc/min ($3.3 \times 10^{-7}$ m³/s) $N_2$ overnight at 175° C., then HF and $N_2$ were co-fed to the reactor at flow rates of 50 cc/min ($8.3 \times 10^{-7}$ m³/s) each at 175° C. After 1.3 h, the nitrogen flow was decreased to 20 cc/min ($3.3 \times 10^{-7}$ m³/s) and the HF flow increased to 80 cc/min ($6.3 \times 10^{-6}$ m³/s). The reactor temperature was gradually increased to 375° C. over a 2 hour period, then treated with 10 cc/min $N_2$ ($1.7 \times 10^{-7}$ m³/s) and 90 cc/min ($1.5 \times 10^{-6}$ m³/s) HF at 409° C. for an additional 2.3 hour. At the end of this period, the HF flow was stopped and the reactor cooled to 300° C. under 20 sccm ($3.3 \times 10^{-7}$ m³/s) nitrogen flow.

The catalyst prepared as above was placed in the reactor, purged with nitrogen and HF at 325° C. The reactor temperature was adjusted to 375° C. and HF and tetrachloroethylene vapor were fed to the reactor in molar ratio of 6:1 at a contact time of 15 seconds. Analysis of the reactor effluent by GC-MS is given below.

| Component | Mole % |
|---|---|
| HFC-125 | 0.1 |
| HCFC-124 | 1.9 |
| HCFC-124a | 0.3 |
| CFC-114a | 1.6 |
| HCFC-123 | 8.6 |
| HCFC-123a | 1.4 |
| HCFC-122 | 2.8 |
| CFC-1112a | 2.5 |
| CFC-1111 | 9.8 |
| HCC-1110 | 68.5 |

Other products included CFC-112, CFC-112a, CFC-113a, CFC-113, CFC-114a, HCFC-133a, HFC-23

Example 23

Fluorination of a Mixture of $CF_3CF_2CHCl_2$ and $CClF_2CF_2CHClF$

Cobalt-substituted chromium oxide (Cr/Co 97/3, 28.57 g, 20 mL,–12 to +20 mesh, (1.68 to 0.84 mm)), prepared as described in PREPARATION EXAMPLE 10, was placed in a ⅝" (1.58 cm) diameter Inconel™ nickel alloy reactor tube heated in a fluidized sand bath. The catalyst was purged with 25 cc/min ($4.2 \times 10^{-7}$ m³/s) nitrogen at 150C for 16 hours. The $N_2$ flow was increased to 50 cc/min ($8.3 \times 10^{-7}$ m³/s) at 175° C. for 0.5 hour. $N_2$ and HF were then co-fed to the reactor at flow rates of 50 cc/min ($8.3 \times 10^{-7}$ m³/s) each. After 1.2 hours, the nitrogen flow was decreased to 20 cc/min ($3.3 \times 10^{-7}$ m³/s) and the HF flow increased to 80 cc/min ($1.3 \times 10^{-6}$ m³/s). The reactor temperature was gradually increased to 300° C. over a 5.7 hours period. The HF was turned off and the reactor purged with 20 cc/min ($3.3 \times 10^{-7}$ m³/s) nitrogen for about 16 hours. The flows of $N_2$ and HF were then established at 20 cc/min ($3.3 \times 10^{-7}$ m³/s) and 80 cc/min ($1.3 \times 10^{-6}$ m³/s), respectively, and the reactor temperature increased from 298° C. to 410° C. over 3.5 hours and then held at 410° C. for 2.3 hours. At the end of this period, the HF flow was stopped and the reactor cooled to 300° C. under 20 sccm ($3.3 \times 10^{-7}$ m³/s) nitrogen flow.

The reactor temperature was adjusted to 325° C. and the vapor of HF and the HCFC-225 cb/ca mixture (52.8 GC area % 225 cb and 46.8 GC area % 225 ca) were co-fed to the reactor in molar ratio of 4:1 at a contact time of 30 seconds. Analysis of the reactor effluent by GC-MS is given below.

| Component | GC Area % |
|---|---|
| HCFC-225ca | 7.5 |
| HCFC-225cb | 16.7 |
| HCFC-224ca | 4.0 |
| HCFC-226ca | 22.6 |
| HCFC-226cb | 30.2 |
| HFC-227ca | 14.8 |

Other products included CFC-217ca, HCFC-226ba, HCFC-226da, HCFC-1224, CFC-216, HCFC-225 isomers, CFC-215ca, HCFC-1223.

Example 24

Fluorination of $CF_3CCl=CCl_2$

Cobalt-substituted chromium oxide (Cr/Co 98/2, 28.04 g, 20 mL, −12 to +20 mesh, (1.68 to 0.84 mm)), prepared as described in Preparation Example 5, was placed in a ⅝" (1.58 cm) diameter Inconel™ nickel alloy reactor tube heated in a fluidized sand bath. The catalyst was heated from 90° C. to 177° C. in a flow of nitrogen (50 cc/min, $8.3 \times 10^{-7}$ $m^3/s$) over the course of about 0.7 hour. HF and $N_2$ were then co-fed to the reactor at flow rates of 50 cc/min ($8.3 \times 10^{-7}$ $m^3/s$) each. After 2 h, the nitrogen flow was decreased to 20 cc/min ($3.3 \times 10^{-7}$ $m^3/s$) and the HF flow increased to 80 cc/min ($1.3 \times 10^{-6}$ $m^3/s$). The reactor temperature was gradually increased to 298° C. during a 3.5 hour period. The HF was turned off and the reactor purged with 20 cc/min ($3.3 \times 10^{-7}$ $m^3/s$) $N_2$ overnight at 299° C. The following day, the $N_2$ and HF flows were established at 20 cc/min ($1.3 \times 10^{-7}$ $m^3/s$) and 80 cc/min ($1.3 \times 10^{-6}$ $m^3/s$), respectively, and the reactor temperature increased to 400° C. over 1.7 hours. The reactor was held at 400–410° C. for an additional 1.3 hours. At the end of this period, the HF flow was stopped and the reactor cooled to 300° C. under 20 sccm ($3.3 \times 10^{-7}$ $m^3/s$) nitrogen flow. HF and CFC-1213xa were then co-fed to the reactor as vapors in molar ratio of 20:1 at a contact time of 15 seconds. Analysis of the reactor effluent by GC-MS at a reactor temperature of 300° C. is given below.

| Component | GC Area % |
|---|---|
| HCFC-226da | 90.0 |
| CFC-216ba | 0.2 |
| CFC-216aa | 4.3 |
| CFC-217ba | 1.0 |
| CFC-1215 | 1.1 |

Other products included HFC-1225, CFC-217ca, CFC-114, CFC-114a, CFC-113, CFC-215, HCFC-225da.

Example 25

Fluorination of $CF_3CCl=CCl_2$

Cobalt/chromium oxide (Cr/Co 98/2, calcined at 550° C., 32.0 g, 20 mL, −12 to +20 mesh, (1.68 to 0.84 mm)), prepared as described in PREPARATION EXAMPLE 6, was placed in a ⅝" (1.58 cm) diameter Inconel™ nickel alloy reactor tube heated in a fluidized sand bath. The catalyst was heated from 65° C. to 176° C. in a flow of nitrogen (50 cc/min, $8.3 \times 10^{-7}$ $m^3/s$) over the course of about 0.8 hour. HF and $N_2$ were then co-fed to the reactor at flow rates of 50 cc/min ($8.3 \times 10^{-7}$ $m^3/s$) each. After 0.6 hour the $N_2$ and HF flows were then adjusted to 20 cc/min ($3.3 \times 10^{-7}$ $m^3/s$) and 80 cc/min ($1.3 \times 10^{-6}$ $m^3/s$), respectively while the reactor temperature was increased to 411° C. over 3 hours. The catalyst was held at 411° C. for 0.75 hour. The $N_2$ and HF flows were then adjusted to 10 cc/min ($1.7 \times 10^{-7}$ $m^3/s$) and 50 cc/min ($8.3 \times 10^{-7}$ $m^3/s$), respectively, while the reactor temperature was maintained at 411° C. for an additional 2 hours. At the end of this period, the HF flow was stopped and the reactor cooled to 295° C. under 15 sccm ($2.5 \times 10^{-7}$ $m^3/s$) nitrogen flow. Hydrogen fluoride and CFC-1213xa were co-fed to the reactor in a molar ratio of 20:1 at a contact time of 15 seconds. Analysis of the reactor effluent by GC-MS is given below.

| Component | GC Area % 300° C. |
|---|---|
| HCFC-226da | 25.4 |
| CFC-216aa | 20.8 |
| CFC-1215 | 35.7 |
| CFC-1214's | 10.0 |
| CFC-217ba | 0.9 |
| CFC-215aa | 1.5 |
| CFC-215bb | 1.7 |
| CFC-1213xa | 2.4 |

Other products included HFP, CFC-216ba, CFC-216cb, CFC-114, CFC-114a, CFC-113, CFC-112.

Comparative Example 26

Fluorination of $CF_3CCl=CCl_2$

A commercial sample of cobalt chromite ($CoCr_2O_4$, CAS Reg. No. [12016-69-2], 40.8 g, 20 mL, −12 to +20 mesh, (1.68 to 0.84 mm)),) was pelletized, sieved, and placed in a ⅝" (1.58 cm) diameter Inconel™ nickel alloy reactor tube heated in a fluidized sand bath. The catalyst was heated from 80° C. to 174° C. in a flow of nitrogen (50 cc/min, $8.3 \times 10^{-7}$ $m^3/s$) over the course of about 1.5 hours. HF and $N_2$ were then co-fed to the reactor at flow rates of 50 cc/min ($8.3 \times 10^{-7}$ $m^3/s$) each. After 0.2 hour, the $N_2$ and HF flows were then adjusted to 20 cc/min ($3.3 \times 10^{-7}$ $m^3/s$) and 80 cc/min ($1.3 \times 10^{-6}$ $m^3/s$), respectively. The catalyst was then heated from 175° C. to 401° C. over the course of 3.2 hours. The HF flow was then ceased and the reactor cooled to 300° C. under 20 sccm ($3.3 \times 10^{-7}$ $m^3/s$) nitrogen flow. Hydrogen fluoride and CFC-1213xa were co-fed to the reactor in a molar ratio of 20:1 with a contact time of 15 seconds. Analysis of the reactor effluent by GC-MS is given below.

| Component | GC Area % 300° C. |
|---|---|
| CFC-1213xa | 97.9 |
| CFC-112 | 0.5 |
| CFC-215aa | 0.2 |
| CFC-1214's | 0.5 |
| CFC-1215 | 0.9 |

Example 27

Chlorofluorination of Ethylene

The catalyst used in this experiment was that used in Example 24. The reactor temperature was adjusted to 250° C. and the vapor of HF, ethylene, and chlorine were co-fed to the reactor in molar ratio of 12:1:1 at a contact time of 15 seconds. The GC-MS analysis of the reactor effluent at 250° C. is shown below.

| Component | GC Area % |
|---|---|
| Ethylene | 6.1 |
| HFC-1141 | 11.4 |
| HFC-152a | 47.3 |
| HCC-1140 | 33.4 |

Other products included HFC-143a, $COF_2$, HCFC-142, HCC-1130, HCC-150.

Example 28

Chlorofluorination of Ethane

The cobalt-substituted chromium oxide from Example 27 was used in this experiment. The reactor temperature was adjusted to 350° C. and HF, CFC-1213xa, and chlorine were co-fed to the reactor in molar ratio of 10:1:4 at a contact time of 15 seconds. Analysis of the reactor effluent by GC-MS at a reactor temperature of 350° C. is given below.

| Component | GC Area % |
|---|---|
| HCFC-133a | 37.0 |
| HFC-143a | 2.1 |
| HFC-134 | 1.6 |
| HCC-1120 | 22.9 |
| HCC-1130 (two) | 19.7 |
| HCC-1140 | 1.3 |
| HCC-1110 | 7.2 |
| CFC-1111 | 1.2 |

Other products included HFC-1141, CFC-115, CFC-114a, HCFC-123a, HCFC-132a.

Example 29

Chlorofluorination of $CF_3CCl=CCl_2$

Cobalt chromium oxide (Cr/Co 99/1, 29.0 g, 20 mL,−12 to +20 mesh, (1.68 to 0.84 mm)), prepared as described in Preparation Example 2, was placed in a ⅝" (1.58 cm) diameter Inconel™ nickel alloy reactor tube heated in a fluidized sand bath. The catalyst was heated from 52° C. to 174° C. in a flow of nitrogen (50 cc/min, 8.3×10$^{-7}$ m$^3$/s) over the course of about one hour. HF and $N_2$ were then co-fed to the reactor at flow rates of 50 cc/min (8.3×10$^{-7}$ m$^3$/s) each for 2 hours; during this time there was a noticeable exotherm. The nitrogen flow was then decreased to 20 cc/min (3.3×10$^{-7}$ m$^3$/s) and the HF flow increased to 80 cc/min (1.3×10$^6$ m$^3$/s). The reactor temperature was gradually increased to 407° C. during a 3 hour period and held at 406° C. for 1.3 hours. The HF flow was then stopped and the reactor cooled to 300° C. under 20 sccm nitrogen flow. Chlorofluorination of CFC-1213xa began at 300° C. with HF, CFC-1213xa, and chlorine co-fed to the reactor with a contact time of 15 seconds. GC-MS analysis of the reactor effluent at 320° C. with a molar ratio of 20:1:4 (for HF, CFC-1213xa, and chlorine, respectively) and at 400° C. with a molar ratio of 30:1:2 are given below.

| | GC Area % | |
|---|---|---|
| Component | 320° C. | 400° C. |
| HCFC-226da | 1.4 | 0.03 |
| CFC-216ba | 21.1 | 8.9 |
| CFC-216aa | 21.9 | 40.8 |
| CFC-217ba | 16.8 | 47.4 |
| CFC-215aa | 35.9 | 0.1 |
| CFC-217ca | 0.7 | 2.0 |
| CFC-216cb | 1.0 | — |

Other products included CFC-1215, CFC-114, CFC-114a, HCFC-225da, CFC-113.

Example 30

Chlorofluorination of $CF_3CCl=CCl_2$

Cobalt/chromium oxide (Cr/Co 95/5, 21.8 g, 15 mL,−12 to +20 mesh, (1.68 to 0.84 mm)), prepared as described in Preparation Example 13 was placed in a ⅝" (1.58 cm) diameter Inconel™ nickel alloy reactor tube heated in a fluidized sand bath. The catalyst was heated from 52° C. to 173° C. in a flow of nitrogen (50 cc/min, 8.3×10$^{-7}$ m$^3$/s) over the course of about 1 hour. HF and nitrogen were then co-fed to the reactor at flow rates of 2 cc/min (4.2×10$^{-7}$ m$^3$/s) and 75 cc/min (1.25×10$^{-6}$M$^3$/s), respectively. After 2.2 hours, the nitrogen and HF flow rates were adjusted to 50 cc/min (8.3×10$^{-7}$ m$^3$/s) each and the reactor temperature was gradually increased to 299° C. over 3 hours. The reactor was purged with 20 cc/min (3.3×10$^{-7}$ m$^3$/s) nitrogen overnight at 299° C. HF and nitrogen were then co-fed to the reactor at 80 cc/min (1.3×10$^{-6}$ m$^3$% s) and 20 cc/min (3.3×10$^{-7}$ m$^3$/s), respectively for 0.6 hour. The temperature of the reactor was then increased to 400° C. over 2 hours. The nitrogen flow was reduced to 10 cc/min (1.7×10$^{-7}$ m$^3$/s) and the temperature increased to 410° C. After 1 hour, the temperature was adjusted to 280° C. Chlorofluorination of CFC-1213xa was begun at 280° C. with HF, CFC-1213xa, and chlorine co-fed to the reactor in a molar ratio of 20:1:4 at a contact time of 15 seconds. GC-MS analyses of the reactor effluent at 320° C. and 350° C. are given below.

| | GC Area Percent | |
|---|---|---|
| Component | 320° C. | 350° C. |
| HCFC-226da | 1.2 | 0.4 |
| CFC-216ba | 23.2 | 26.6 |
| CFC-216aa | 19.5 | 35.3 |
| CFC-217ba | 8.7 | 9.8 |
| CFC-215aa | 44.5 | 25.8 |

Other products included CFC-217ca, CFC-1215, CFC-115, CFC-13, CFC-114, CFC-114a, CFC-216cb, CFC-113, CFC-214, CFC-215.

Example 31

Chlorofluorination of $CF_3CCl=CCl_2$

Cobalt/chromium oxide pre-treated with excess ammonium nitrate (Cr/Co 95/5, 21.8 g, 15 mL,−12 to +20 mesh, (1.68 to 0.84 mm)), prepared as described in Preparation Example 15 was placed in a ⅝" (1.58 cm) diameter Inconel™ nickel alloy reactor tube heated in a fluidized sand bath. The catalyst was heated from 77° C. to 200° C. in a flow of nitrogen (25 cc/min, 4.2×10⁻⁷ m³/s) over the course of about 1.3 hours and held at this temperature for about 63 hours. HF and nitrogen were then co-fed to the reactor at flow rates of 50 cc/min (8.3×10⁻⁷ m³/s) each at 177° C. After 1.6 hours, the HF and nitrogen flow rates were adjusted to 80 cc/min (1.3×10⁻⁶ m³/s) and 20 cc/min (3.3×10⁻⁷ m³/s), respectively, and the temperature of the reactor increased to 413° C. over 5 hours. After 0.7 hour at 413° C., the HF flow was stopped and the reactor purged with nitrogen overnight at 300° C. Chlorofluorination of CFC-1213xa was begun at 300° C. with HF, CFC-1213xa, and chlorine co-fed to the reactor in a molar ratio of 20:1:4 at a contact time of 15 seconds. The GC-MS analyses of the reactor effluent at molar feed ratios of 20:1:4 at 320° C. and 350° C. and at 350° C. with a molar feed ratio of 30:1:2 are given below.

| | GC Area Percent | | |
|---|---|---|---|
| Component | 320° C. 20:1:4 | 350° C. 20:1:4 | 350° C. 30:1:2 |
| HCFC-226da | 1.8 | 0.9 | 3.0 |
| CFC-216ba | 17.6 | 18.6 | 12.2 |
| CFC-216aa | 22.5 | 34.1 | 42.9 |
| CFC-217ba | 18.1 | 20.4 | 27.6 |
| CFC-215aa | 36.7 | 23.8 | 12.0 |

Other products included CFC-217ca, CFC-1215, CFC-115, CFC-114, CFC-114a, CFC-216cb, CFC-113, CFC-214, CFC-215.

Example 32

Chlorofluorination of CF₃CCl=CCl₂

Cobalt/chromium oxide (Cr/Co 97/3, 31.6 g, 20 mL,–12 to +20 mesh, (1.68 to 0.84 mm)), prepared as described in Preparation Example 11 was placed in a ⅝" (1.58 cm) diameter Inconel™ nickel alloy reactor tube heated in a fluidized sand bath. The catalyst was heated from 47° C. to 174° C. in a flow of nitrogen (50 cc/min, 8.3×10⁻⁷ m³/S) over the course of about 0.8 hour. HF and nitrogen were then co-fed to the reactor at flow rates of 50 cc/min (8.3×10⁻⁷ m³/s) each. After 0.7 hours, the nitrogen and HF flow rates were adjusted to 20 cc/min (3.3×10⁻⁷ m³/s) and 80 cc/min (1.3×10⁻⁶ m³/s), respectively. After 1.7 hours at 175° C., the reactor temperature was gradually increased to 410° C. over 3.4 hours. After 1 hour, the temperature was reduced from 410° C. to 298° C., the HF flow shut off, and the reactor purged with nitrogen over night. Chlorofluorination of CFC-1213xa was begun at 300° C. with HF, CFC-1213xa, and chlorine vapor co-fed to the reactor in a molar ratio of 20:1:4 at a contact time of 15 seconds. The GC-MS analyses of the reactor effluent at 320° C. and 350° C. with molar feed ratios of 20:1:4 and at 400° C. with molar feed ratios of 30:1:2 are given below.

| | GC Area Percent | | |
|---|---|---|---|
| Component | 320° C. | 350° C. | 400° C. |
| HCFC-226da | 3.0 | 1.8 | 1.1 |
| CFC-216ba | 17.1 | 24.7 | 19.6 |
| CFC-216aa | 14.6 | 19.6 | 33.7 |
| CFC-217ba | 14.9 | 21.0 | 31.7 |
| CFC-215aa | 44.1 | 29.6 | 10.6 |
| CFC-215bb | 3.7 | 0.03 | — |

Other products included CFC-217ca, CFC-1215, CFC-115, CFC-13, CFC-114, CFC-114a, CFC-216cb, CFC-113, CFC-214, CFC-215.

Example 33

Chlorofluorination of CF₃CCl=CCl₂

Cobalt/chromium oxide (Cr/Co 97/3, 28.2 g, 20 mL,–12 to +20 mesh, (1.68 to 0.84 mm)), prepared as described in Preparation Example 10 was placed in a ⅝" (1.58 cm) diameter Inconel™ nickel alloy reactor tube heated in a fluidized sand bath. The catalyst was purged with 25 cc/min (8.3×10⁻⁷ m³/s) nitrogen at 150C for 16 hours. The N₂ flow was increased to 50 cc/min (8.3×10⁻⁷ m³/s) at 175C for 0.5 hour. N₂ and HF were then co-fed to the reactor at flow rates of 50 cc/min (8.3×10⁻⁷ m³/s) each. After 1.2 hours, the nitrogen flow was decreased to 20 cc/min (3.3×10⁻⁷ m³/s) and the HF flow increased to 80 cc/min. The reactor temperature was gradually increased to 300° C. over a 5.7 hours period. The HF was turned off and the reactor purged with 20 cc/min (3.3×10⁻⁷ m³/s) nitrogen for about 16 hours at 300° C. The flows of N₂ and HF were then established at 20 cc/min (3.3×10⁻⁷ m³/s) and 80 cc/min (1.3×10⁻⁶ m³/s), respectively, and the reactor temperature increased from 298° C. to 410° C. over 3.5 hours and then held at 410° C. for 2.3 hours. At the end of this period, the HF flow was stopped and the reactor cooled to 300° C. under 20 sccm nitrogen flow. Chlorofluorination of CFC-1213xa was begun at 300° C. with HF, CFC-1213xa, and chlorine vapor co-fed to the reactor in a molar ratio of 20:1:4 at a contact time of 15 seconds. The GC-MS analyses of the reactor effluent at 320° C. and 350° C. are given below.

| | GC Area Percent | |
|---|---|---|
| Component | 320° C. | 350° C. |
| HCFC-226da | 2.0 | 1.0 |
| CFC-216ba | 16.8 | 21.2 |
| CFC-216aa | 26.4 | 32.5 |
| CFC-217ba | 14.2 | 19.7 |
| CFC-215aa | 36.4 | 23.1 |

Other products included CFC-217ca, CFC-1215, HFC-1225, CFC-115, CFC-13, CFC-114, CFC-114a, CFC-216cb, CFC-113.

Example 34

Chlorofluorination of CF₃CCl=CCl₂

Cobalt/chromium oxide (Cr/Co 98/2, calcined at 400° C., 21.06 g, 15 mL,–12 to +20 mesh, (1.68 to 0.84 mm)), prepared as described in PREPARATION EXAMPLE 3, was placed in a ⅝" (1.58 cm) diameter Inconel™ nickel alloy reactor tube heated in a fluidized sand bath. The catalyst was heated from 77° C. to 176° C. in a flow of nitrogen (50 cc/min, 8.3×10⁻⁷ m³/s) over the course of about 1.7 hours. HF and N₂ were then co-fed to the reactor at flow rates of 50 cc/min (8.3×10⁻⁷ m³/s) each. After 1 hour the temperature was increased to 326° C. over 3 hour while maintaining the HF and N₂ flows at 50 cc/min (8.3×10⁻⁷ m³/s). The N₂ and HF flows were then adjusted to 25 cc/min (4.2×10⁻⁷ m³/s) and 50 cc/min (8.3×10⁻⁷ m³/s), respectively, while the reactor temperature was increased to 401° C. over 1 hour. The N₂ and HF flows were then adjusted to 10 cc/min and 50 cc/min (8.3×10⁻⁷ m³/s), respectively, while the reactor temperature was maintained at 401° C. for 1 hour. At the end of this period, the HF flow was stopped and the reactor cooled to 280° C. under 20 sccm nitrogen flow. Chlorofluorination of CFC-1213xa was begun at 280° C.

with HF, CFC-1213xa, and chlorine vapor co-fed to the reactor in a molar ratio of 20:1:4 at a contact time of 15 seconds. The GC-MS data for the reactor effluent at 320° C. (20:1:4) and at 400° C. (molar feed ratio 30:1:2; contact time=15 second) are given below.

|  | GC Area Percent | |
| --- | --- | --- |
| Component | 320° C. | 400° C. |
| HCFC-226da | 1.7 | 0.02 |
| CFC-216ba | 23.1 | 4.9 |
| CFC-216aa | 19.0 | 46.4 |
| CFC-216cb | 0.4 | — |
| CFC-217ba | 15.3 | 46.6 |
| CFC-215aa | 38.3 | 0.03 |
| CFC-215bb | 0.1 | — |
| CFC-214ab | — | — |

Other products included CFC-217ca, CFC-1215, CFC-115, CFC-114, CFC-114a, CFC-113, CFC-1213xa, CFC-112

Example 35

Chlorofluorination of $CF_3CCl{=}CCl_2$

Cobalt/chromium oxide (Cr/Co 98/2, calcined at 900° C., 27.52 g, 15 mL, −12 to +20 mesh, (1.68 to 0.84 mm)), prepared as described in Preparation Example 4, was placed in a ⅝" (1.58 cm) diameter Inconel™ nickel alloy reactor tube heated in a fluidized sand bath. The catalyst was heated from 96° C. to 174° C. in a flow of nitrogen (50 cc/min, $8.3 \times 10^{-7}$ m$^3$/s) over the course of about 0.5 hour. HF and N$_2$ were then co-fed to the reactor at flow rates of 50 cc/min ($8.3 \times 10^{-7}$ m$^3$/s) each. After 0.3 hour at 175° C., the flows of HF and N$_2$ were adjusted to 80 cc/min ($1.3 \times 10^{-7}$ m$^3$/s) and 20 cc/min ($3.3 \times 10^{-7}$ m$^3$/s), respectively, and the temperature was then increased to 400° C. over 5 hours. At the end of this period, the HF flow was stopped and the reactor cooled to 300° C. under 20 sccm ($3.3 \times 10^{-7}$ m$^3$/s) nitrogen flow. Chlorofluorination of CFC-1213xa was begun at 300° C. with HF, CFC-1213xa, and chlorine vapor co-fed to the reactor in a molar ratio of 20:1:4 at a contact time of 15 seconds. The GC-MS analyses of the reactor effluent at 320° C. and 400° C. are given below.

|  | GC Area Percent | |
| --- | --- | --- |
| Component | 320° C. | 400° C. |
| HCFC-226da | 0.4 | 0.1 |
| CFC-216ba | 9.2 | 34.9 |
| CFC-216aa | 19.6 | 26.6 |
| CFC-216cb | 2.0 | 2.4 |
| CFC-217ba | 10.4 | 14.8 |
| CFC-215aa | 23.9 | 17.5 |
| CFC-215bb | 28.6 | 1.6 |
| CFC-214ab | 3.4 | 0.04 |

Other products included CFC-217ca, CFC-1215, CFC-115, CFC-114, CFC-114a, CFC-113, CFC-1213xa, CFC-112

Example 36

Chlorofluorination of $CF_3CCl{=}CCl_2$

Hydrogen fluoride, CFC-1213xa, and chlorine were co-fed to the reactor containing the catalyst in Example 25 with a contact time of 15 seconds. The GC-MS analyses of the reactor effluent at 320° C. (molar ratio of feed gases HF:1213xa:Cl$_2$=20:1:4) and 375° C. (molar ratio of feed gases HF:1213xa:Cl$_2$=30:1:2) are given below.

|  | GC Area Percent | |
| --- | --- | --- |
| Component | 320° C. | 375° C. |
| CFC-217ba | 11.0 | 22.1 |
| CFC-216aa | 22.4 | 27.5 |
| CFC-216ba | 15.5 | 33.8 |
| CFC-216cb | 2.3 | 3.1 |
| HCFC-226da | 0.7 | 0.5 |
| CFC-215aa | 27.6 | 9.6 |
| CFC-215bb | 18.9 | 1.5 |
| CFC-1213xa | — | — |

Other products included CFC-115, CFC-217ca, CFC-1215, CFC-114, CFC-114a, CFC-1214's, CFC-113, CFC-112, CFC-214ab.

Example 37

Chlorofluorination of $CF_3CCl{=}CCl_2$

Cobalt/chromium oxide (Cr/Co 98/2, calcined at 550° C., 29.4 g, 20 mL, −12 to +20 mesh, (1.68 to 0.84 mm)), prepared as described in Preparation Example 9, was placed in a ⅝" (1.58 cm) diameter Inconel™ nickel alloy reactor tube heated in a fluidized sand bath. The catalyst was purged with nitrogen (50 cc/min, $8.3 \times 10^{-7}$ m$^3$/s) at 174° C. for about 72 hours. HF and N$_2$ were then co-fed to the reactor at flow rates of 50 cc/min ($8.3 \times 10^{-7}$ m$^3$/s) each. After 0.8 hour at 175° C., the flows of HF and N$_2$ were adjusted to 80 cc/min ($1.3 \times 10^{-6}$ m$^3$/s) and 20 cc/min ($3.3 \times 10^{-7}$ m$^3$/s), respectively, and the temperature was then increased to 400° C. over 4.3 hours. The flows of HF and N$_2$ were adjusted to 50 cc/min ($8.3 \times 10^{-7}$ m$^3$% s) and 10 cc/min ($1.7 \times 10^{-7}$ m$^3$/s), respectively, and the reactor held at 406° C. for an additional 1.7 hours. At the end of this period, the HF flow was stopped and the reactor cooled to 300° C. under 20 sccm ($3.3 \times 10^{-7}$ m$^3$/s) nitrogen flow. Chlorofluorination of CFC-1213xa was begun at 300° C. with HF, CFC-1213xa, and chlorine vapor co-fed to the reactor in a molar ratio of 20:1:4 at a contact time of 15 seconds. The GC-MS analyses of the reactor effluent at 300° C. (molar ratio of feed gases HF:1213xa:Cl$_2$=20:1:4) and 400° C. (molar ratio of feed gases HF:1213xa:Cl$_2$=30:1:2) are given below.

|  | GC Area Percent | |
| --- | --- | --- |
| Component | 300° C. | 400° C. |
| CFC-217ba | 11.1 | 36.7 |
| CFC-216aa | 18.7 | 36.6 |
| CFC-216ba | 18.4 | 21.7 |
| CFC-216cb | 1.6 | — |
| HCFC-226da | 1.3 | 0.2 |
| CFC-215aa | 44.8 | 2.6 |
| CFC-215bb | 2.6 | — |
| CFC-1213xa | — | — |

Other products included FC-218, CFC-13, CFC-115, CFC-217ca, CFC-1215, CFC-114, CFC-114a, CFC-1214's, CFC-113, CFC-214ab.

Comparative Example 38

Chlorofluorination of $CF_3CCl=CCl_2$

Hydrogen fluoride, CFC-1213xa, and chlorine were co-fed to the reactor containing the HF-treated cobalt chromite catalyst from Comparative Example 26; the contact time of 15 seconds. The GC-MS analysis of the reactor effluent at 375° C. (molar ratio of feed gases HF:1213xa:$Cl_2$=20:1:4) is given below.

| Component | GC Area Percent 375° C. |
|---|---|
| CFC-217ba | 0.2 |
| CFC-216aa | 0.6 |
| CFC-216ba | 0.4 |
| CFC-216cb | 3.1 |
| CFC-215aa | 10.5 |
| CFC-215bb | 24.9 |
| CFC-214ab | 27.4 |
| CFC-1215 | 1.0 |
| CFC-1214's | 12.5 |
| CFC-1213xa | 21.6 |

Other products included CFC-115, CFC-216cb, CFC-114, CFC-114a, CFC-1214's, CFC-112, CFC-214ab.

Comparative Example 39

Chlorofluorination of $CF_3CCl=CCl_2$ 100% Chromium (III) oxide (calcined at 400° C., 27.8 g, 20 mL,–12 to +20 mesh, (1.68 to 0.84 mm)), prepared as described in Comparative Preparation Example 1 was placed in a ⅝" (1.58 cm) diameter Inconel™ nickel alloy reactor tube heated in a fluidized sand bath. The catalyst was heated from 77° C. to 200° C. in a flow of nitrogen (50 cc/min, 8.3×10$^{-7}$ m$^3$/s) over the course of about an hour. The catalyst was then purged overnight with nitrogen (20 cc/min, 3.3×10$^{-7}$ m$^3$/s) at 174° C. HF and nitrogen were then co-fed to the reactor at flow rates of 50 cc/min (8.3×10$^{-7}$ m$^3$/s) each at 175° C. After an hour, the HF and nitrogen flow rates were adjusted to 80 cc/min (1.3×10$^4$ m$^3$/s) and 20 cc/min (3.3×10$^{-7}$ m$^3$/s), respectively, and the temperature of the reactor increased to 410° C. over 3.6 hours. The HF flow was stopped and the reactor purged with nitrogen overnight at 300° C. Chlorofluorination of CFC-1213xa was begun at 300° C. with HF, CFC-1213xa, and chlorine vapor co-fed to the reactor in a molar ratio of 20:1:4 at a contact time of 15 seconds. The GC-MS analyses of the reactor effluent at 300° C. and at 400° C. (molar feed ratio=30:1:2) are given below.

| | GC Area Percent | |
|---|---|---|
| Component | 300° C. | 400° C. |
| HCFC-226da | 2.4 | 0.03 |
| CFC-216ba | 21.6 | 6.4 |
| CFC-216aa | 19.8 | 67.4 |
| CFC-217ba | 11.1 | 24.1 |
| CFC-217ca | 0.4 | 1.2 |
| CFC-215aa | 42.9 | 0.2 |

Other products included FC-218, CFC-1215, CFC-115, CFC-114, CFC-114a, CFC-216cb, CFC-113, CFC-112.

Example 40

Isomerization of a 1:1 $CF_3CClFCClF_2$/$CF_3CCl_2CF_3$ Mixture

The catalyst used in Example 34 was returned to the reactor and purged with nitrogen up to 350° C. A mixture of CFC-216ba/216aa (50.2 GC area % 216ba and 49.8 GC area % 216aa) and nitrogen were then co-fed to the reactor in molar ratio of 1:4 with a contact time of 30 seconds. The GC-MS analyses of the reactor effluent are given below.

| Component | GC Area % |
|---|---|
| CFC-216ba | 0.75 |
| CFC-216aa | 84.0 |
| CFC-217ba | 7.6 |
| CFC-215aa | 1.0 |
| CFC-1213xa | 3.9 |
| CFC-1215 | 0.60 |

Other products included CFC-115, FC-218, CFC-217ca, CFC-114, CFC-114a, CFC-216cb, HCFC-226da, HCFC-225da, CFC-1214, CFC-215bb.

Example 41

Fluorination of a $CF_3CHClF$/$CClF_2CHF_2$ Mixture

Cobalt-substituted chromium oxide (Cr/Co 95/5, 29.04 g, 20 mL,–12 to +20 mesh, (1.68 to 0.84 mm)), prepared as described in PREPARATION EXAMPLE 15 was placed in a ⅝" (1.58 cm) diameter Inconel™ nickel alloy reactor tube heated in a fluidized sand bath. The catalyst was heated from 77° C. to 175° C. in a flow of nitrogen (25 cc/min, 3.3×10$^{-7}$ m$^3$/s) over the course of about 1.2 hours. HF and nitrogen were then co-fed to the reactor at a flow rate of 50 cc/min (8.3×10$^{-7}$ m$^3$/s) each. After 1.5 hours, the nitrogen flow was decreased to 20 cc/min (3.3×10$^{-7}$ m$^3$/s) and the HF flow increased to 80 cc/min (1.3×10$^{-6}$ m$^3$/s). The reactor temperature was gradually increased to 413° C. during a 5 hour period and maintained at 413° C. for an additional 0.6 hour. At the end of this period, the HF flow was stopped and the reactor cooled to 300° C. under 20 sccm nitrogen flow. HF and a mixture of HCFC-124 and HCFC-124a (52.1 GC area % 124a and 44.2 GC area % 124) vapor were co-fed to the reactor in molar ratio of 4:1 at a contact time of 10 seconds. The GC-MS analysis of the reactor effluent at 300° C. is given below.

| Component | Mole % |
|---|---|
| HFC-125 | 44.1 |
| HCFC-124 | 24.7 |
| HCFC-124a | 25.0 |
| CFC-133a | 0.9 |
| HCFC-123 | 2.7 |

Other products included impurities in starting material: HFC-32, HFC-143a, HFC-134a, HFC-134 and by-products: HFC-23, CFC-115, CFC-114a, HCFC-123a, HCFC-123b, CFC-113.

Example 42

Disproportionation of a CF$_3$CHClF/CClF$_2$CHF$_2$ Mixture

Nitrogen and a mixture of HCFC-124 and HCFC-124a (52.1 GC area % 124a and 44.2 GC area % 124) were co-fed to the reactor containing the catalyst used in Example 41. The molar ratio of nitrogen to 124/124a mixture was 4:1 and the contact time was 10 seconds. The GC-MS analyses of the reactor effluent at 250° C. and 300° C. are given below.

|  | GC Mole % | |
| --- | --- | --- |
| Component | 250° C. | 300° C. |
| HFC-125 | 24.6 | 55.2 |
| HCFC-124 | 19.9 | 12.1 |
| HCFC-124a | 37.7 | 1.7 |
| CFC-133a | 1.6 | 2.1 |
| HCFC-123 | 13.9 | 18.1 |
| HCFC-123a | 0.3 | 0 |
| HCC-1110 | — | 4.7 |
| HCC-1120 | 0.8 | 1.7 |
| CFC-1111 | 0.2 | 2.5 |

Other products included HFC-23, HFC-32 HFC-143a, CFC-115, CFC-114a, HCFC-123b, CFC-113, HCFC-122.

Example 43

Isomerization and Disproportionation of a CClF$_2$CCl$_2$F/CF$_3$CCl$_3$ Mixture Nitrogen and a mixture of CFC-113 and CFC-113a (52.9 GC mole % 113a and 47.1 GC mole % 113) were co-fed to the reactor containing the catalyst used in Example 42. The molar ratio of nitrogen to 113/113a mixture was 4:1 and the contact time was 15 seconds. The GC-MS analyses of the reactor effluent at 150° C. and 300° C. are given below.

|  | Mole % | |
| --- | --- | --- |
| Component | 150° C. | 300° C. |
| CFC-115 | — | 1.7 |
| CFC-114 | — | 6.2 |
| CFC-114a | 21.2 | 24.5 |
| CFC-1112a | 10.4 | 8.5 |
| CFC-113 | 27.2 | 10.4 |
| CFC-113a | 30.0 | 33.3 |
| CFC-112/112a | 10.7 | 9.8 |
| HCC-1110 | 0.03 | 4.7 |

Other products included CFC-13, HCFC-1122, CFC-1113, CFC-1111, CFC-1316.

Example 44

Disproportionation of CF$_3$CCl$_2$F

Nitrogen and CFC-114a (99.95 GC mole % 114a) were co-fed to the reactor containing the catalyst used in EXAMPLE 43 in a molar ratio of 4:1 with a contact time of 15 seconds. The GC-MS analyses of the reactor effluent at 250° C. and 350° C. are given below.

|  | Mole % | |
| --- | --- | --- |
| Component | 250° C. | 350° C. |
| CFC-115 | 18.5 | 38.1 |
| CFC-114 | — | 2.3 |
| CFC-114a | 64.6 | 30.6 |
| CFC-1112a | 0.2 | 0.7 |
| CFC-113 | 0.03 | 0.7 |
| CFC-113a | 15.8 | 24.6 |
| CFC-112/112a | — | 0.2 |
| HCC-1110 | 0.04 | 1.8 |

Other products included CFC-13, FC-116, HCFC-1122, CFC-1113, HCFC-123, CFC-1111, CFC-1316.

Example 45

Disproportionation and Isomerization of a CClF$_2$CClF$_2$/CF$_3$CClF$_2$ Mixture Nitrogen and a mixture of CFC-114 and CFC-114a (87.3 GC mole % 114 and 12.6 GC mole % 114a) were co-fed to the reactor containing the catalyst used in EXAMPLE 44. The molar ratio of nitrogen to 114/114a mixture was 4:1 and the contact time was 15 seconds. The GC-MS analyses of the reactor effluent at 300° C. and 350° C. are given below.

|  | Mole % | |
| --- | --- | --- |
| Component | 300° C. | 350° C. |
| CFC-115 | 13.6 | 30.5 |
| CFC-114 | 65.9 | 34.0 |
| CFC-114a | 11.0 | 18.1 |
| CFC-1112a | 1.4 | 1.9 |
| CFC-113 | 4.8 | 4.4 |
| CFC-113a | 2.0 | 6.6 |
| CFC-112/112a | 0.2 | 0.4 |
| HCC-1110 | 0.4 | 3.0 |

Other products included HFC-23, CFC-13, FC-116, HCFC-1122, CFC-1113, CFC-1111.

Example 46

CF$_3$CH$_2$CF$_3$ Dehydrofluorination

Nitrogen and HFC-236fa were co-fed to the reactor containing the catalyst used in EXAMPLE 45. The molar ratio of nitrogen to 236fa was 4:1 and the contact time was 15 seconds. The GC-MS analyses of the reactor effluent at 300° C. and 350° C. are given below.

|  | Mole % | |
| --- | --- | --- |
| Component | 300° C. | 350° C. |
| HFC-236fa | 91.0 | 81.5 |
| HFC-1225zc | 7.2 | 17.1 |

Other products included HFC-143a, CFC-1215, HCFC-226da, HCFC-1224, HCFC-1326, HCFC-1223, CFC-216aa, CFC-217ba.

Example 47

CH$_3$CHF$_2$ Dehydrofluorination

Nitrogen and HFC-152a were co-fed to the reactor containing the catalyst used in Example 45. The molar ratio of nitrogen to 152a was 4:1 and the contact time was 15 seconds. The GC-MS analyses of the reactor effluent at 250° C. and 350° C. are given below.

|  | Mole % | |
| --- | --- | --- |
| Component | 250° C. | 350° C. |
| HFC-152a | 63.1 | 16.7 |
| HFC-1141 | 36.4 | 82.0 |

Other products included HCFC-151a, HCC-1140, ethylene, methane.

Example 48

Isomerization of Hexafluorocyclopropane

The catalyst used in Example 34 (15 mL, 21.35 g) was returned to the reactor and purged with nitrogen at 350° C. followed by HCl. Nitrogen and hexafluorocyclopropane were then co-fed to the reactor in a 2:1 molar ratio; the contact time was 30 seconds. The GC-MS analysis of the reactor effluent at 150° C. is given below.

| Component | GC Area % 150° C. |
| --- | --- |
| HFP | 98.0 |
| TFE | 1.1 |
| HFC-23 | 0.4 |
| HFC-227ea | 0.2 |

Other products included HFC-125, CFC-217ba, FC-1318my, PFIB, CFC-1215's.

Example 49

Chlorodefluorination of Trifluoromethane

The catalyst used in Example 33 (5 mL, 7.1 g) was returned to the reactor and purged with nitrogen at 300° C. Anhydrous hydrogen chloride and trifluoromethane (HFC-23) were then co-fed to the reactor in a 20:1 molar ratio; the contact time was 5 seconds. The GC-MS analysis of the reactor effluent at 325° C. is given below.

| Component | GC Area % |
| --- | --- |
| HFC-23 | 71.9 |
| HCFC-22 | 6.3 |
| HCFC-21 | 2.6 |
| HCC-20 | 18.2 |
| CFC-13 | 0.7 |
| CFC-12 | 0.2 |

Example 50

Chlorodefluorination of 1,1,1,3,3,3-Hexafluoropropane

Anhydrous hydrogen chloride and 1,1,1,3,3,3-hexafluoropropane (HFC-236fa) were co-fed in a 10:1 molar ratio to the reactor containing the catalyst used in EXAMPLE 49; the contact time was 10 seconds. The GC-MS analysis of the reactor effluent at 325° C. is given below.

| Component | GC Area % |
| --- | --- |
| HFC-236fa | 49.8 |
| HFC-1225zc | 0.9 |
| HCFC-1224 (two) | 4.0 |
| HCFC-235fa | 0.7 |
| HCFC-1223za | 40.0 |
| CFC-1213xa | 3.7 |

Other products included HFC-143a, CFC-114/114a, CFC-1214, HCC-1120, HCFC-1222, HCC-1110.

Additional Catalyst Preparation

Preparation Example 51

Preparation of 98% Chromium/2% Cobalt (550° C.)

[Cr(NH$_3$)$_6$]Cl$_3$] (16.7684 g, 64.4 mmoles) and [Co(NH$_3$)$_6$]Cl$_3$] (0.3513 g, 1.31 mmole) were dissolved in deionized water. Aqueous ammonium hydroxide was then added to the solution until precipitation was complete. The resulting precipitate was filtered and dried in air at 110° C. for 12 hours. The resulting product was ground thoroughly in an agate mortar and then heated at 550° C. in air for 12 hours.

Analysis of the sample by XRD indicated a predominant phase having α-Cr$_2$O$_3$ structure; and TEM and EDS indicated a small amount of a spinel phase containing cobalt and chromium. The cobalt-containing α-Cr$_2$O$_3$ phase was present in the form of 200–400 nm crystals. XAS indicated that cobalt was completely incorporated into the α-Cr$_2$O$_3$ lattice.

What is claimed is:

1. A crystalline colbalt-substituted alpha-chromium oxide where from about 0.05 atom % to about 6 atom % of the chromium atoms in the alpha-chromium oxide lattice are replaced by trivalent cobalt atoms.

2. A chromium-containing catalyst composition comprising as a chromium-containing component the crystalline cobalt-substituted alpha-chromium oxide of claim 1.

3. A chromium-containing catalyst composition comprising a chromium-containing component prepared by treating the crystalline cobalt-substituted alpha-chromium oxide of claim 1 with a fluorinating agent.

4. A method for preparing a composition comprising the crystalline cobalt-substituted alpha-chromium oxide of claim 1, comprising:

(a) co-precipitating a solid by adding ammonium hydroxide to an aqueous solution of a soluble cobalt salt and a soluble trivalent chromium salt that contains at least three moles of nitrate per mole of chromium in the solution and has a cobalt concentration of from about 0.05 mole % to about 6 mole % of the total concentration of cobalt and chromium in the solution; and after at east three moles of ammonium per mole of chromium in the solution has been added to the solution;

(b) collecting co-precipitated solid formed in (a);

(c) drying the collected solid; and (d) calcining the dried solid in the presence of oxygen.

5. The method of claim 4 wherein the soluble cobalt salt is a divalent cobalt salt.

6. The method of claim 5 wherein the soluble cobalt and chromium salts are nitrates or hydrated nitrates.

7. The method of claim 6 wherein more than three moles of ammonium nitrate per mole of chromium is present in the aqueous solution.

8. The method of claim 4 wherein a mixture comprising co-precipitated solid and ammonium nitrate from (a) is dried and calcined.

9. The method of claim 8 wherein the dried solid is calcined in air.

10. The method of claim 4 wherein the dried solid is calcined in air.

11. A process for changing the fluorine distribution in a hydrocarbon or a halogenated hydrocarbon, characterized by:

bringing said hydrocarbon or a halogenated hydrocarbon into the presence of a catalyst composition comprising at least one chromium-containing component selected from the group consisting of the crystalline cobalt-substituted alpha-chromium oxide of claim 1 and a crystalline cobalt-substituted alpha-chromium oxide of claim 1 which has been treated with a fluorinating agent.

12. The process of claim 11 wherein the fluorine distribution in a halogenated hydrocarbon compound is changed by isomerizing said halogenated hydrocarbon compound in the presence of said catalyst composition.

13. The process of claim 11 wherein the fluorine distribution in a halogenated hydrocarbon compound is changed by disproportionating said halogenated hydrocarbon compound in the vapor phase in the presence of said catalyst composition.

14. A process for increasing the fluorine content of a halogenated hydrocarbon compound or an unsaturated hydrocarbon compound comprising:

reacting said compound with hydrogen fluoride in the vapor phase in the presence of a catalyst composition comprising at least one chromium-containing component selected from the group consisting of the crystalline cobalt-substituted alpha-chromium oxide of claim 1 and a crystalline cobalt-substituted alpha-chromium oxide of claim 1 which has been treated with a fluorinating agent.

15. A process for increasing the fluorine content of a halogenated hydrocarbon compound or a hydrocarbon compound comprising:

reacting said compound with HF and $Cl_2$ in the vapor phase in the presence of a catalyst composition comprising at least one chromium-containing component selected from the group consisting of the crystalline cobalt-substituted alpha-chromium oxide of claim 1 and a crystalline cobalt-substituted alpha-chromium oxide of claim 1 which has been treated with a fluorinating agent.

16. A process for decreasing the fluorine content of a halogenated hydrocarbon compound:

dehydrofluorinating said halogenated hydrocarbon compound in the presence of a catalyst composition comprising at least one chromium-containing component selected from the group consisting of the crystalline cobalt-substituted alpha-chromium oxide of claim 1 and a crystalline cobalt-substituted alpha-chromium oxide of claim 1 which has been treated with a fluorinating agent.

17. The A process for decreasing the fluorine content of a halogenated hydrocarbon compound comprising:

reacting said halogenated hydrocarbon compound with hydrogen chloride in the vapor phase in the presence of a catalyst composition comprising at least one chromium-containing component selected from the group consisting of the crystalline cobalt-substituted alpha-chromium oxide of claim 1 and a crystalline cobalt-substituted alpha-chromium oxide of claim 1 which has been treated with a fluorinating agent.

* * * * *